(12) United States Patent
McGrath et al.

(10) Patent No.: US 9,579,224 B2
(45) Date of Patent: Feb. 28, 2017

(54) VESSEL REMODELING METHODS AND DEVICES FOR USE IN A GRAFT DEVICE

(75) Inventors: Jon McGrath, Duxbury, MA (US); Mohammed S. El-Kurdi, Mansfield, MA (US); Lorenzo Soletti, Pittsburgh, PA (US); J. Christopher Flaherty, Auburndale, FL (US)

(73) Assignee: Neograft Technologies, Inc., Taunton, MA (US)

( * ) Notice: Subject to any disclaimer, the term of this patent is extended or adjusted under 35 U.S.C. 154(b) by 0 days.

(21) Appl. No.: 14/234,974

(22) PCT Filed: Jul. 24, 2012

(86) PCT No.: PCT/US2012/047996
§ 371 (c)(1),
(2), (4) Date: Mar. 25, 2014

(87) PCT Pub. No.: WO2013/016349
PCT Pub. Date: Jan. 31, 2013

(65) Prior Publication Data
US 2014/0303715 A1 Oct. 9, 2014

Related U.S. Application Data

(60) Provisional application No. 61/511,312, filed on Jul. 25, 2011.

(51) Int. Cl.
*A61B 17/11* (2006.01)
*A61F 2/82* (2013.01)
(Continued)

(52) U.S. Cl.
CPC .......... *A61F 2/82* (2013.01); *A61B 17/00008* (2013.01); *A61B 17/11* (2013.01);
(Continued)

(58) Field of Classification Search
CPC .... A61F 2/2412; A61F 2/2418; A61F 2/2469; A61F 2/2475; A61F 2/24
(Continued)

(56) References Cited

U.S. PATENT DOCUMENTS 4,033,337 A * 7/1977 Raczkowski ................ 600/499
5,718,973 A * 2/1998 Lewis ................ A61F 2/82
428/35.7
(Continued)

FOREIGN PATENT DOCUMENTS

CN 1491728 4/2004
JP 2004525272 8/2004
(Continued)

OTHER PUBLICATIONS

Gusic et al, Shear Stress and Pressure Modulate Saphenous Vein Remodeling Ex Vivo, Journal of Biomechanics 38 (2005), pp. 1760-1767.*

(Continued)

*Primary Examiner* — Thomas J Sweet
*Assistant Examiner* — Wade P Schutte
(74) *Attorney, Agent, or Firm* — Wilson Sonsini Goodrich & Rosati

(57) ABSTRACT

Methods and devices for treating a vessel for use in a medical procedure are disclosed. A vein or other vessel can be modified in situ, prior to harvesting. Subsequently, at least a portion of the vessel is removed, and subsequently implanted to treat a patient, typically in a bypass procedure in which the vessel portion fluidly connects a source of oxygenated blood to an occluded artery.

38 Claims, 13 Drawing Sheets

(51) Int. Cl.

| | | |
|---|---|---|
| A61L 27/36 | (2006.01) | |
| A61L 27/50 | (2006.01) | |
| A61B 17/00 | (2006.01) | |
| A61B 17/135 | (2006.01) | |
| A61B 17/22 | (2006.01) | |

(52) U.S. Cl.
CPC ........ *A61B 17/135* (2013.01); *A61L 27/3625* (2013.01); *A61L 27/3687* (2013.01); *A61L 27/3691* (2013.01); *A61L 27/507* (2013.01); *A61B 2017/00778* (2013.01); *A61B 2017/00969* (2013.01); *A61B 2017/1107* (2013.01); *A61B 2017/1132* (2013.01); *A61B 2017/22097* (2013.01)

(58) Field of Classification Search
USPC .......................................................... 128/898
See application file for complete search history.

(56) References Cited

U.S. PATENT DOCUMENTS

| | | | |
|---|---|---|---|
| 5,813,167 | A | 9/1998 | Hoshino et al. |
| 6,035,856 | A * | 3/2000 | LaFontaine et al. ......... 128/898 |
| 6,036,702 | A | 3/2000 | Bachinski et al. |
| 6,165,212 | A | 12/2000 | Dereume et al. |
| 6,187,038 | B1 | 2/2001 | Sullivan et al. |
| 6,296,863 | B1 | 10/2001 | Trogolo et al. |
| 6,440,163 | B1 | 8/2002 | Swanson et al. |
| 6,599,323 | B2 | 7/2003 | Melican et al. |
| 6,891,077 | B2 | 5/2005 | Rothwell et al. |
| 7,037,332 | B2 | 5/2006 | Kutryk et al. |
| 7,374,774 | B2 | 5/2008 | Bowlin et al. |
| 7,452,374 | B2 | 11/2008 | Hain et al. |
| 7,531,503 | B2 | 5/2009 | Atala et al. |
| 7,759,099 | B2 | 7/2010 | Wolf et al. |
| 7,759,120 | B2 | 7/2010 | Wolf et al. |
| 7,794,219 | B2 | 9/2010 | Dubson et al. |
| 7,833,267 | B2 | 11/2010 | Flagle et al. |
| 7,905,826 | B2 | 3/2011 | Case et al. |
| 7,998,188 | B2 | 8/2011 | Zilla et al. |
| 8,057,537 | B2 | 11/2011 | Zilla et al. |
| 8,172,746 | B2 | 5/2012 | Zilla et al. |
| 8,353,814 | B2 | 1/2013 | Villafana et al. |
| 8,491,457 | B2 | 7/2013 | Atala et al. |
| 8,992,594 | B2 | 3/2015 | Soletti et al. |
| 2002/0042128 | A1 | 4/2002 | Bowlin et al. |
| 2002/0123786 | A1 | 9/2002 | Gittings et al. |
| 2003/0109887 | A1 | 6/2003 | Galdonik et al. |
| 2004/0058887 | A1 | 3/2004 | Bowlin et al. |
| 2004/0094873 | A1 | 5/2004 | Dubson et al. |
| 2004/0146546 | A1 | 7/2004 | Gravett et al. |
| 2004/0171545 | A1 | 9/2004 | Chaikof et al. |
| 2004/0219185 | A1 | 11/2004 | Ringeisen |
| 2005/0002998 | A1 | 1/2005 | Chang et al. |
| 2005/0203636 | A1 | 9/2005 | McFetridge |
| 2006/0085063 | A1 | 4/2006 | Shastri et al. |
| 2006/0204441 | A1 | 9/2006 | Atala et al. |
| 2006/0240061 | A1 | 10/2006 | Atala et al. |
| 2007/0004961 | A1 | 1/2007 | Case et al. |
| 2007/0173917 | A1 | 7/2007 | Hayashi et al. |
| 2007/0239267 | A1 | 10/2007 | Hendriks et al. |
| 2007/0293932 | A1 | 12/2007 | Zilla et al. |
| 2008/0208323 | A1 | 8/2008 | El-Kurdi et al. |
| 2009/0012607 | A1 | 1/2009 | Kim et al. |
| 2009/0048669 | A1 | 2/2009 | Flagle et al. |
| 2010/0160718 | A1 | 6/2010 | Villafana et al. |
| 2010/0280598 | A1 | 11/2010 | Fox |
| 2010/0331964 | A1 | 12/2010 | Clerin et al. |
| 2011/0087337 | A1 * | 4/2011 | Forsell ............ A61B 17/12 623/23.68 |
| 2011/0230955 | A1 * | 9/2011 | Orion ............ A61F 2/064 623/1.15 |
| 2012/0116495 | A1 | 5/2012 | Zilla et al. |
| 2014/0296767 | A1 * | 10/2014 | Franano ............ A61M 1/32 604/8 |

FOREIGN PATENT DOCUMENTS

| | | | |
|---|---|---|---|
| JP | 2006526658 | 11/2006 | |
| WO | 9832367 | 7/1998 | |
| WO | WO 98/32367 A2 | 7/1998 | |
| WO | 2004028583 | 4/2004 | |
| WO | 2006044904 | 4/2006 | |
| WO | 2010042721 | 4/2010 | |
| WO | WO2010058406 A1 * | 5/2010 | ............... A61F 2/06 |
| WO | WO 2012/097229 A2 | 7/2012 | |

OTHER PUBLICATIONS

Soletti et al., A Bi-layered Elastomeric Scaffold for Tissue Engineering of Small-Diameter Vascular Grafts, Acta Biomater., Jan. 2010, pp. 110-122, 6(1).

Southgate et al., Involvement of Extracellular-Matrix-Degrading Metalloproteinases in Rabbit Aortic Smooth-Muscle Cell Proliferation, Biochem. J., 1992, pp. 93-99, 288.

Stankus et al., Fabrication of Biodegradable Elastomeric Scaffolds with Sub-Micron Morphologies, J. Biomed. Mater Res., 2004, pp. 603-614, 70A.

Stankus et al., Microintegrating Smooth Muscle Cells into a Biodegradable, Elastomeric Fiber Matrix, Biomaterials, 2006, pp. 735-744, 27.

Stankus et al., Fabrication of Cell Microintegrated Blood Vessel Constructs Through Electrohydrodynamic Atomization, Biomaterials, 2007, pp. 2738-2746, 28.

Stocker et al., Pressure-Diameter Relationship in the Human Greater Saphenous Vein, Ann. Thorac. Surg., 2003, pp. 1533-1538, 76.

Szilagyi et al., Biologic Fate of Autogenous Vein Implants as Arterial Substitutes: Clinical, Angiographic and Histopathologic Observations in Femoro-Popliteal Operations for Atherosclerosis, Ann. Surg., Sep. 1973, pp. D232-D246, 178(3).

Tai et al., Compliance Properties of Conduits Used in Vascular Reconstruction, Br. J. Surg., 2000, pp. 1516-1524, 87.

Tu et al., Migfilin and Mig-2 Link Focal Adhesions to Filamin and the Actin Cytoskeleton and Function in Cell Shape Modulation, Cell., Apr. 14, 2003, pp. 37-47, 113.

Tyagi et al., Stretch-Induced Membrane Type Matrix Metalloproteinase and Tissue Plasminogen Activator in Cardiac Fibroblast Cells, J. Cell Physiol., 1998, pp. 374-382, 176.

Uzui et al., The Role of Protein-Tyrosine Phosphorylation and Gelatinase Production in the Migration and Proliferation of Smooth Muscle Cells, Atherosclerosis, 2000, pp. 51-59, 149.

Veazey et al., Mammalian Cell Delivery via Aerosol Deposition, J. Biomed. Mater. Res. Part B, 2005, pp. 334-338, 72B.

Vijayan et al., External Supports and the Prevention of Neointima Formation in Vein Grafts, Eur. J. Vasc. Endovasc. Surg., 2002, pp. 13-22,24.

Vijayan et al., Long-Term Reduction of Medial and Intimal Thickening in Porcine Saphenous Vein Grafts with a Polyglactin Biodegradable External Sheath, J. Vasc. Surg., 2004, pp. 1011-1019,40.

Vorp et al., Modeling the Transmural Stress Distribution During Healing of Bioresorbable Vascular Prostheses, Ann. Biomed. Eng., 1995, pp. 178-188, 23.

Vorp et al., A Device for the Application of Cyclic Twist and Extension on Perfused Vascular Segments, Am. J. Physiol., 1996, pp. H787-H795, 270.

Wang et al., Expression of Apoptosis-Related Proteins and Structural Features of Cell Death in Explanted Aortocoronary Saphenous Vein Bypass Grafts, Cardiovasc. Surg., 2001, pp. 319-328, 9(4).

Wang et al., Regulation of Vein Graft Hyperplasia by Survivin, an Inhibitor of Apoptosis Protein, Arterioscler. Throm b. Vasc. Biol., Aug. 25, 2005, pp. 2081-2087, 25.

Wesly et al., Static Linear and Nonlinear Elastic Properties of Normal and Arterialized Venous Tissue in Dog and Man, Circ. Res., 1975, pp. 509-520, 37.

Wolf et al., Antibodies Against Transforming Growth Factor-Beta 1 Suppress Intimal Hyperplasia in a Rat Model, J. Clin. Invest., 1994, pp. 1172-1178, 93.

(56) References Cited

OTHER PUBLICATIONS

Wolff et al.. Transforming Growth Factor-Beta1 Antisense Treatement of Rat Vein Grafts Reduces the Accumulation of Collagen and Increases the Accumulation of H-Caldesmon, J. Vasc. Surg., 2006, pp. 1028-1036, 43.

Wu et al., Integrin-Linked Kinase (ILK) and its Interactors: A New Paradigm for the Coupling of Extracellular Matrix to Actin Cytoskeleton and Signaling Complexes, J. Cell. Bioi., Nov. 12, 2001, pp. 505-510, 155(4).

Wu, Integrin-Linked Kinase and PINCH: Partners in Regulation of Cell-Extracellular Matrix Interaction and Signal Transduction, J. Cell. Sci., 1999, pp. 4485-4489, 112.

Xu et al., Aligned Biodegradable Nanofibrous Structure: A Potential Scaffold for Blood Vessel Engineering, Biomaterials, 2004, pp. 877-886, 25.

Yamaoka et al., TIMP-1 Production by Human Scleral Fibroblast Decreases in Response to Cyclic Mechanical Stretching, Opthalmic Research, 2001, pp. 98-101, 33.

Zhang et al., Association of Smooth Muscle Cell Phenotypic Modulation with Extracellular Matrix Alterations During Neointima Formation in Rabbit Vein Grafts, J. Vasc. Surg., 1999, pp. 169-183, 30.

Zuckerbraun et al., Overexpression of Mutated 1-kappa B-alpha Inhibits Vascular Smooth Muscle Cell Proliferation and Intimal Hyperplasia Formation, J. Vasc. Surg., 2003, pp. 812-819, 38.

Zwolak et al., Kinetics of Vein Graft Hyperplasia: Association with Tangential Stress, Journal of Vasc. Surg., 1987, pp. 126-136, 5.

Alcocer et al., Mutual Exclusion of Apoptosis and HSP 70 in Human Vein Intimal Hyperplasia In Vitro, J. Surg. Res. 2001, pp. 75-80,96.

Angelini et al., Distention Promotes Platelet and Leukocyte Adhesion and Reduces Short-Term Patency in Pig Arteriovenous Bypass Grafts, J. Thorac. Cardiovasc. Surg., 1990, pp. 433-439,99.

Annabi et al., Differential Regulation of Matrix Metalloproteinase Activities in Abdominal Aortic Aneurysms, J. Vasc. Surg., 2002, pp. 539-546, 35.

Asanuma et al., Uniaxial Strain Upregulates Matrix-Degrading Enzymes Produced by Human Vascular Smooth Muscle Cells, Am. J. Physiol. Heart Circ. Physiol., 2003, pp. H1778-H1784, 284.

Bandyk et al., The Failing Graft: An Evolving Concept, Semin. Vasc. Surg., Jun. 1993, pp. 75-77, 6(2).

Bassiouny et al., Anastomotic Intimal Hyperplasia: Mechanical Injury or Flow Induced, J. Vasc. Surg., 1992, pp. 708-717, 15.

Bassiouny et al., Low Flow Enhances Platelet Activation After Acute Experimental Arterial Injury, J. Vasc. Surg., 1998, pp. 910-918, 27.

Berkowitz et al., Reversed Vein Graft Stenosis: Early Diagnosis and Management, J. Vasc. Surg., 1992, pp. 130-142, 15.

Bornstein, Diversity of Function is Inherent in Matricellular Proteins: An Appraisal of Thrombospondin 1, J. Cell. Biol., Aug. 1995, pp. 503-506, 130(3).

Brant et al., Measurement In Vitro of Pulsatile Arterial Diameter Using a Helium-Neon Laser, J. Appl. Physiol., 1987, pp. 679-683, 62(2).

Bunt, Synthetic Vascular Graft Infections. I. Graft Infections, Surgery, 1983, pp. 733-746, 93(6).

Cabrera Fischer et al., Reduced Elastic Mismatch Achieved by Interposing Vein Cuff in Expanded Polytetrafluoroethylene Femoral Bypass Decreases Intimal Hyperplasia, Artif. Organs, 2005, pp. 122-130, 29(2).

Cagiannos et al., Rapamycin-Coated Expanded Polytetrafluoroethylene Bypass Grafts Exhibit Decreased Anastomotic Neointimal Hyperplasia in a Porcine Model, J. Vasc. Surg., Nov. 2005, pp. 980-988, 42(5).

Campbell et al., Arterial Smooth Muscle, A Multifunctional Mesenchymal Cell. Arch Pathol. Lab Med., Oct. 1988, pp. 977-986, 112(10).

Campbell et al., Vein Grafts for Arterial Repair: Their Success and Reasons for Failure, Ann. R. Coli. Surg. Engl., 1981, pp. 257-260, 63.

Cho et al., Matrix Metalloproteinase-9 is Necessary for the Regulation of Smooth Muscle Cell Replication and Migration After Arterial Injury, Circ. Res. 2002, pp. 845-851, 91.

Davies et al., Prevention of Malignment During Non-Reversed Femorodistal Bypass, Ann. R. Coli. Surg. Engl., 1992, pp. 434-435, 74.

Davies et al., Pre-Bypass Morphological Changes in Vein Grafts, Eur. J. Vasc. Surg., 1993, pp. 642-647, 7.

Dethlefsen et al., Comparison of the Effects of Mechanical Stimulation on Venous and Arterial Smooth Muscle Cells In Vitro, J. Vasc. Res., 1996, pp. 405-413,33.

Dobrin et al., Mechanical Factors Predisposing to Intimal Hyperplasia and Medial Thickening in Autogenous Vein Grafts, Surgery, 1989, pp. 393-400, 105.

Ducasse et al., Interposition Vein Cuff and Intimal Hyperplasia: An Experimental Study, Eur. J. Vasc. Endovasc. Surg., 2004, pp. 617-621, 27.

Edwards et al., Primary Graft Infections, J. Vasc. Surg., 1987, pp. 235-239,6.

Francis et al., Release of Platelet-Derived Growth Factor Activity from Pig Venous Arterial Grafts, J. Thorac. Cardiovasc. Surg., 1994, pp. 540-548, 108.

Fuchs et al., Postoperative Changes in Autologous Vein Grafts, Ann Surg., Jul. 1978, pp. 1-15, 188(1).

Fujimoto et al., In Vivo Evaluation of a Porous, Elastic, Biodegradable Patch for Reconstructive Cardiac Procedures, Ann Thorac. Surg., 2007, pp. 648-654, 83.

Fujimoto et al., An Elastic, Biodegradable Cardiac Patch Induces Contractile Smooth Muscle and Improves Cardiac Remodeling and Function in Subacute Myocardial Infarction, J. Am. Coli. Cardiolo., 2007, pp. 2292-3000, 49(23).

Galis et al., Cytokine-Stimulated Human Vascular Smooth Muscle Cells Synthesize a Complement of Enzymes Required for Extracellular Matrix Digestion, Circulation Research, 1994, pp. 181-189, 75.

Garanich et al., Shear Stress Inhibits Smooth Muscle Cell Migration via Nitric Oxide-Mediated Downregulation of Matrix Metalloproteinase-2 Activity, Am. J. Physiol. Heart Circ. Physiol., 2005, pp. H2244-H2252, 288.

George et al., Gene Transfer of Tissue Inhibitor of Metalloproteinase-2 Inhibits Metalloproteinase Activity and Neointima Formation in Human Saphenous Veins, Gene Ther, 1998, pp. 1552-1560, 5.

George et al., Adenovirus-Mediated Gene Transfer of the Human TIMP-1 Gene Inhibits Smooth Muscle Cell Migration and Neointimal Formation in Human Saphenous Vein, Hum. Gene Ther., Apr. 10, 1998, pp. 867-877,9.

George et al., Surgical Preparative Injury and Neointima Formation Increase MMP-9 Expression and MMP-2 Activation in Human Saphenous Vein, Cardiovasc. Res., 1997, pp. 447-459, 33.

Goldman et al., Degradation of Alpha-Actin Filaments in Venous Smooth Muscle Cells in Response to Mechanical Stretch, Am. J. Physiol. Heart Circ. Physiol., 2003, pp. H1839-H1847, 284.

Goldman et al.. Negative Regulation of Vascular Smooth Muscle Cell Migration by Blood Shear Stress, Am. J. Physiol. Heart Circ. Physiol., 2007, pp. H928-H938, 292.

Greenwood et al., Restructuring of Focal Adhesion Plaques by Pi 3-Kinase: Regulation by PtdIns (3,4,5)-P3 Binding to Alpha-Actinin, J. Cell. Bioi., Aug. 7, 2000, pp. 627-641, 150(3).

Grote et al., Mechanical Stretch Enhances mRNA Expression and Proenzyme Release of Matrix Metalloproteinase-2 (MMP-2) via NAD(P)H Oxidase-Derived Reactive Oxygen Species, Circulation Research, 2003, pp. e80-e86, 92.

Guan et al., Synthesis, Characterization, and Cytocompatibility of Elastomeric, Biodegradable Poly(ester-urethane) ureas Based on Poly(caprolactone) and Putrescine, J. Biomed. Mater Res., 2002, pp. 493-503, 61.

Gusic et al., Shear Stress and Pressure Modulate Saphenous Vein Remodeling Ex Vivo, J. Biomech., 2005, pp. 1760-1769, 38.

Hayashi, Experimental Approaches on Measuring the Mechanical Properties and Constitutive Laws of Arterial Walls, J. Biomech. Eng., Nov. 1993, pp. 481-488, 115.

(56) References Cited

OTHER PUBLICATIONS

He et al., Arterial Replacement with Compliant Hierarchic Hybrid Vascular Graft: Biomechanical Adaptation and Failure Tissue Engineering, 2002, pp. 213-224, 8(2).
Hilker et al., Bypass Graft Disease: Analysis of Proliferative Activity in Human Aorto-Coronary Bypass Grafts, Heart Surg. Forum, 2002, pp. S331-S341, 5 Suppl. 4.
Hu et al., Activation of PDGF Receptor Alpha in Vascular Smooth Muscle Cells by Mechanical Stress, Faseb J., 1998, pp. 1135-1142, 12.
Huynh et al., Alterations in Wall Tension and Shear Stress Modulate Tyrosine Kinase Signaling and Wall Remodeling in Experimental Vein Grafts, J. Vasc. Surg., 1999, pp. 334-344,29.
Huynh et al., External Support Modulates G Protein Expression and Receptor Coupling in Experimental Vein Grafts, Surgery, Aug. 1999, pp. 127-134, 126(2).
Igase et al., Apoptosis and Bcl-xs in the Intimal Thickening of Balloon-Injured Carotid Arteries, Clin. Sci. (Land.), 1999, pp. 605-612, 96.
Jacot et al., Early Adaptation of Human Lower Extremity Vein Grafts: Wall Stiffness Changes Accompany Geometric Remodeling, J. Vasc. Surg., Mar. 2004, pp. 547-555, 39(3).
Jankowski-Bell, "Histology of Blood Vessels", available at http://www2.victoriacollege.edu/dept/bio/Belltutorials/Histology%20Tutorial/Blood%20Vessels/Histology_of_Blood_Vessels.html. Oct. 2006, 7 pages.
Jeremy et al., A Bioabsorbable (polyglactin), Nonrestrictive, External Sheath Inhibits Porcine Saphenous Vein Graft Thickening, J. Thorac Cardiovasc., Surg., Jun. 2004, pp. 1766-1772, 127(6).
Jeremy et al., Nitric Oxide Synthase and Adenylyl and Guanylyl Cyclase Activity in Porcine Interposition Vein Grafts, Ann. Thorac. Surg., 1997, pp. 470-476, 63.
Jiang et al., Wall Shear Modulation of Cytokines in Early Vein Grafts, J. Vasc. Surg., 2004, pp. 345-350, 40.
Jiang et al., A Novel Vein Graft Model: Adaptation to Differential Flow Enviornments, Am. J. Physiol. Heart Circ. Physiol., 2004, pp. H240-H245, 286.
Kamenz et al.. Incidence of Intimal Proliferation and Apoptosis Following Balloon Angioplasty in an Atherosclerotic Rabbit Model. Cardiovasc. Res., 2000, pp. 766-776, 45.
Kanjickal et al., Polymeric Sustained Local Drug Delivery System for the Prevention of Vascular Intimal Hyperplasia, J. Biomed. Mater Res., 2004, pp. 489-495, 68A.
Karayannacos et al., Late Failure in Vein Grafts: Mediating Factors in Subendothelial Fibromuscular Hyperplasia, Ann. Surg., Feb. 1978, pp. 183-188.
Kohler et al., The effect of Rigid External Support on Vein Graft Adaptation to the Arterial Circulation, J. Vasc. Surg., 1989, pp. 277-285, 9.
Kohler et al., Inhibition of Neointimal Hyperplasia in a Sheep Model of Dialysis Access Failure with the Bioabsorbable Vascular Wrap Paclitaxei-Eiuting Mesh, J. Vasc. Surg. 2007, pp. 1029-1038,45.
Labadie et al., Pulsatile Perfusion System for Ex Vivo Investigation of Biochemical Pathways in Intact Vascular Tissue, Am. J. Physiol., 1996, pp. H760-H768, 270.
Lafleur et al., Activation of Pro-(matrix metalloproteinase-2) (pro-MMP-2) by Thrombin is Membrane-Type-MMP-Dependent in Human Umbilical Vein Endothelial Cells and Generates a Distinct 63 kDa Active Species, Biochem. J., D 2001, pp. 107-115, 357.
Lee et al., Nanofiber Alignment and Direction of Mechanical Strain Affect the ECM Production of Human ACL Fibroblast, Biomaterials, 2005, pp. 1261-1270, 26.
Lee et al., Theoretical Hydraulic Consequences of Vein Graft Taper, J. Vasc. Surg., 2003, pp. 785-792, 38.
Liao et al., A Novel Time-Varying Poly Lactic-Co Glycolic Acid External Sheath for Vein Grafts Designed Under Physiological Loading, Tissue Eng., 2007, pp. 2855-2862, 13(12).
Ligush, Jr. et al., Evaluation of Endothelium-Derived Nitric Oxide Mediated Vasodilation Utilizing Ex Vivo Perfusion of an Intact Vessel, J. Surg. Res., 1992, pp. 416-421,52.
Lijnen et al., Tissue Inhibitor of Matrix Metalloproteinases-1 Impairs Arterial Neointima Formation After Vascular Injury in Mice, Circ. Res., 1999, pp. 1186-1191,85.
Liu et al., The Signaling Protein Rho is necessary for Vascular Smooth Muscle Migration and Survival but not for Proliferation, Surgery, 2002, pp. 317-325, 132.
Liu et al., Changes in the Organization of the Smooth Muscle Cells in Rat Vein Grafts, Ann. Biomed. Eng., 1998, pp. 86-95, 26.
Liu et al., A Possible Role of Initial Cell Death Due to Mechanical Stretch in the Regulation of Subsequent Cell Proliferation in Experimental Vein Grafts, Biomech. Model Mechanobiol., 2002, pp. 17-27, 1.
Liu et al., Partial Prevention of Monocyte and Granulocyte Activation in Experimental Vein Grafts by Using a Biomechanical Engineering Approach, J. Biomech., 1999, pp. 1165-1175, 32.
Mavromatis et al., Early Effects of Arterial Hemodynamic Conditions on Human Saphenous Veins Perfused Ex Vivo, Arterioscler. Thromb. Vasc. Biol., 2000, pp. 1889-1895, 20.
Mehta et al., External Stenting Reduces Long-Term Medial and Neointimal Thickening and Platelet Derived Growth Factor Expression in a Pig Model of Arteriovenous Bypass Grafting, Nat. Med., Feb. 1998, pp. 235-239, 4(2).
Meng et al., Mechanical Stretching of Human Saphenous Vein Grafts Induces Expression and Activation of Matrix-Degrading Enzymes Associated with Vascular Tissue Injury and Repair, Exp. Mol. Pathol., 1999, pp. 227-237, 66.
Mii et al., Transforming Growth Factor-Beta Inhibits Human Vascular Smooth Muscle Cell Growth and Migration, Surgery, 1993, pp. 464-470, 114.
Morinaga et al., Effect of Wall Shear Stress on Intimal Thickening of Arterially Transplanted Autogenous Veins in Dogs, J. Vasc. Surg., 1985, pp. 430-433, 2.
Morisaki et al., Cell Cycle-Dependent Inhibition of DNA Synthesis by Prostaglandin 12 in Cultured Rabbit Aortic Smooth Muscle Cells, Atherosclerosis, 1988, pp. 165-171,71.
Moritz et al.. A Method for Constricting Large Veins for Use in Arterial Vascular Reconstruction, Artificial Organs, 1990, pp. 394-398, 14(5).
Muluk et al., Enhancement of Tissue Factor Expression by Vein Segments Exposed to Coronary Arterial Hemodynamics, J. of Vasc. Surg., 1998, pp. 521-527, 27.
Murphy-Ullrich et al., Focal Adhesion Integrity is Downregulated by the Alternatively Spliced Domain of Human Tenascin., J. Cell Biol., Nov. 1991, pp. 1127-1136, 115(4).
Murphy-Ullrich, The De-adhesive Activity of Matricellular Proteins: Is Intermediate Cell Adhesion an Adaptive State?, J. Clin. Invest., Apr. 2001, pp. 785-790, 107(7).
Nagai et al., Identification of Two Types of Smooth Muscle Myosin Heavy Chain Isoforms by cDNA Cloning and Immunoblot Analysis, The Journal of Biological Chemistry, Jun. 15, 1989, pp. 9734-9737, 264(17).
Nakazawa et al., Smooth Muscle Cell Migration Induced by Shear-Loaded Platelets and Endothelial Cells. Enhanced Platelet-Derived Growth Factor Production by Shear-Loaded Platelets, Int. Angiol., Jun. 2000, pp. 142-146, 19.
Nedovic et al., Cell Immobilisation by Electrostatic Droplet Generation, Landbauforsch Volk., 2002, pp. 11-17, (241).
Newby et al., Extracellular Matrix Degrading Metalloproteinases in the Pathogensis of Arteriosclerosis, Basic Res. Cardiol., 1994, pp. 59-70, 89(Suppl 1).
Nikolopoulos et al., Integrin-Linked Kinase (ILK) Binding to Paxillin LD1 Motif Regulates ILK Localization to Focal Adhesions, J. Biol. Chem., Jun. 29, 2001, pp. 23499-23505, 276(26).
Nishibe et al., Induction of Angiotensin Converting Enzyme in Neointima After Intravascular Stent Placement, Int. Angiol., Sep. 2002, pp. 250-255, 21(3).
Parsonnet et al., New Stent for Support of Veins in Arterial Grafts, Arch. Surg., Oct. 1963, pp. 696-702, 87.

(56) References Cited

OTHER PUBLICATIONS

Pintucci et al., Anti-Proliferative and Anti-Inflammatory Effects of Topical MAPK Inhibition in Arterialized Vein Grafts, Faseb J., 2006, pp. 398-400, 20(2).
Porter et al., Marimastat Inhibits Neointimal Thickening in a Model of Human Vein Graft Stenosis, Br. J. Surg., 1998, pp. 1373-1377, 85.
Porter et al., Simvastatin Inhibits Human Saphenous Vein Neointima Formation via Inhibition of Smooth Muscle Cell Proliferation and Migration, J. Vasc. Surg., 2002, pp. 150-157, 36.
Porter et al., The Development of an In Vitro Flow Model of Human Saphenous Vein Graft Intimal Hyperplasia, Cardiovasc. Res., 1996, pp. 607-614, 31.
Porter et al., Production and Inhibition of the Gelatinolytic Matrix Metalloproteinases in a Human Model of Vein Graft Stenosis, Eur. J. Vasc. Endovasc. Surg., 1999, pp. 404-412, 17.
Powell et al., Matirix-Specific Effect of Endothelial Control of Smooth Muscle Cell Migration, J. Vasc. Surg., 1996, pp. 51-57, 24.
Predel et al., Implications of Pulsatile Stretch on Growth of Saphenous Vein and Mammary Artery Smooth Muscle, Lancet., Oct. 10, 1992, pp. 878-879, 340.
Qian et al., Gene Expression of bFGF and Intimal Hyperplasia of Autologous Vein Grafts in Rats, Nal'l. Med. J. China. Nov. 1996, pp. 826-828, 76(11).
Ramos et al., Histologic Fate and Endothelial Changes of Distended and Nondistended Vein Grafts, Ann. Surg., Mar. 1976, pp. 205-228, 183(3).
Redmond et al., Effect of Pulse Pressure on Vascular Smooth Muscle Cell Migration: The Role of Urokinase and Matrix Metalloproteinase, Thromb. & Haemosl., 1999, pp. 293-300, 81.
Resnick et al., Hemodynamic Forces are Complex Regulators of Endothelial Gene Expression, The Faseb. J., 1995, pp. 874-882, 9.
Rho et al., Electrospinning of Collagen Nanofibers: Effects on the Behavior of Normal Human Keratinocytes and Early-Stage Wound Healing, Biomaterials, 2006, pp. 1452-1461,27.
Sage et al., Extracellular Proteins that Modulate Cell-Matrix Interactions, Spare, Tenascin, and Thrombospondin., J. Biol. Chem., Aug. 15, 1991, pp. 14831-14834, 266(23).
Severyn et al., The Influence of Hemodynamics and Wall Biomechanics on the Thrombogenicity of Vein Segments Perfused In Vitro, J. Surg. Res., 2004, pp. 31-37, 121.
Shigematsu et al., Direct and Indirect Effects of Pulsatile Shear Stress on the Smooth Muscle Cell, Int. Angiol., 2000, pp. 39-46, 19(1).
Sho et al., Subnormal Shear Stress-Induced Intimal Thickening Requires Medial Smooth Muscle Cell Proliferation and Migration, Exp. Mol. Pathol., 2002, pp. 150-160, 72.
Simosa et al., Survivin Expression is Up-Regulated in Vascular Injury and Identifies a Distinct Cellular Phenotype, J. Vasc. Surg., 2005, pp. 682-690,41.
Ayres, et al. Modulation of anisotropy in electrospun tissue-engineering scaffolds: Analysis of fiber alignment by the fast Fourier transform. Biomaterials 27 (2006) 5524-5534.
Ben-Gal, et al. Expandable external support device to improve saphenous vein graft patency after cabg. J Cardiothorac Surg 2013;8:122.
Chakrabarty, S. Fibrin solubilizing properties of certain anionic and cationic detergents. Thrombosis research 55.4 (1989): 511-519.
Courtney, et al. Design and anlysis of tissue engineering scaffolds that mimic soft tissue mechanical anisotropy. Biomaterials. 2006, 27: 3631-3638.
Deitzel, et al. Controlled deposition of electrospun poly(ethylene oxide) fibers. Polymer. 2001, 42: 8163-8170.
Deitzel, et al. The effect of processing variable on the morphology of electrospun nanofibers and textiles. Polymer 42 (2001): 261-272.
Hermans, et al. Fibrin: structure and interactions. Seminars in thrombosis and hemostasis. vol. 8. No. 1. 1982.
International preliminary report on patentability and written opinion dated Feb. 24, 2013 for PCT Application No. US2012/047996.
International search report and written opinion dated Feb. 24, 2013 for PCT Application No. US2012/047996.
Izzat, et al. Influence of external stent size on early medial and neointimal thickening in a pig model of saphenous vein bypass graftin. Circulation 1996; 94:1741-5.
Jankowski-Bell, et al. Histology of Blood Vessels—www2.victoriacollege.edu/dept/bio/Belltutorials/Histology%20Tutorial/Blood%20Vessels/Histology_of_Blood_Vessels.html.
Jeremy, et al. A bioabsorbable (polyglactin), nonrestrictive, external sheath inhibits porcine saphenous vein graft thickening. J Thorac Cardiovasc Surg. 2004;127(6): 1766-72.
Kohler, et al. The effect of rigid external support on vein graft adaptation to the arterial circulation. J Vasc Surg. 1989;9(2): 277-85.
Levorson, et al. Fabrication and characterization of multiscale electrospun scaffolds for cartilage regeneration. Biomed Mater 2013;8:014103. doi:10.1088/1748-6041/8/1/014103.
McManus, et al. Electrospun fibrinogen: feasibility as a tissue engineering scaffold in a rat cell culture model. Journal of Biomedical Materials Research Part A 81.2 (2007): 299-309.
McManus, et al. Mechanical properties of electrospun fibrinogen structures. Acta Biomaterialia 2.1 (2006): 19-28.
Mehta, et al. External stenting reduces long-term medial and neointimal thickening and platelet derived growth factor expression in a pig model of arteriovenous bypass grafting. Nat Med. 1998;4(2): 235-9.
Morton, et al. Electrospun fibrin nanofibers for the use in tissue engineering. Modification of fibrin to improve applications in regenerative medicine (2010): 81.
Mosesson, M.W. Fibrinogen and fibrin structure and functions. Journal of Thrombosis and Haemostasis 3.8 (2005): 1894-1904.
Parsonnet, et al. New stent for support of veins in arterial grafts. Arch Surg. 1963;87: 696702.
Perumcherry, et al. A Novel Method for the Fabrication of Fibrin-Based Electrospun Nanofibrous Scaffold for Tissue-Engineering Applications*. Tissue Engineering Part C: Methods 17.11 (2011): 1121-1130.
Sell, et al. Cross-linking methods of electrospun fibrinogen scaffolds for tissue engineering applications. Biomedical Materials 3.4 (2008): 045001.
Sreerekha, et al. Fabrication of fibrin based electrospun multiscale composite scaffold for tissue engineering applications. Journal of biomedical nanotechnology 9.5 (2013): 790-800.
Stankus, et al. Fabrication of biodegradable elastomeric scaffolds with sub-micron morphologies. J Biomed Mater Res A. 2004;70(4): 603-14.
Stitzel, et al. Controlled fabrication of a biological vascular substitute. Biomaterials. 2006, 27: 1088-1094.
Stooker, et al. Perivenous application of fibrin glue reduces early injury to the human saphenous vein graft wall in an ex vivo model. European Journal of Cardio-thoracic Surgery. 2002, 21: 212-217.
Traver, et al. New Generation Tissue Sealants and Hemostatic Agents. Innovative Urologic Applications. Reviews in Urology. 2006, 8: 104-111.
Vijayan, et al. Long-term reduction of medial and intimal thickening in porcine saphenous vein grafts with a polyglactin biodegradable external sheath. J Vasc Surg. 2004;40(5): 1011-9.
Wan, et al. Differential, time-dependent effects of perivenous application of fibrin glue on medial thickening in porcine saphenous vein grafts. European Journal of Cardio-thoracic Surgery, 29, (2006): 742-747.
Weisel, et al. Computer modeling of fibrin polymerization kinetics correlated with electron microscope and turbidity observations: clot structure and assembly are kinetically controlled. Biophysical journal 63.1 (1992): 111.
Weisel, et al. Mechanisms of fibrin polymerization and clinical implications. Blood 121.10 (2013): 1712-1719.
Wnek, et al. Electrospirming of nanofiber fibrinogen structures. Nano Letters 3.2 (2003): 213-216.
Xu, et al. Electrospun Nanofiber Fabrication as Synthetic Extracellular Matrix and Its Potential for Vascular Tissue Engineering. Tissue Engineering, vol. 10, No. 7/8, 2004.

(56) References Cited

OTHER PUBLICATIONS

Yu, et al. Electrospinning, Encyclopedia of Polymer Science & Technology (2008) 1-20.
Zilla, et al. Constrictive external nitinol meshes inhibit vein graft intimal hyperplasia in nonhuman primates. The Journal of Thoracic and Cardiovascular Surgery 2008;136:717-725.
Zilla, et al. Utilization of shape memory in external vein-graft meshes allows extreme diameter constriction for suppressing intimal hyperplasia: A non-human primate study. J Vasc Surg 2009;49:1532-42.
Castronuovo, J. The sequence of gene expression in cultured human saphenous vein after injury. (2002) J. Vasc. Surg. 35, 146-151.
Fingerle. Intimal lesion formation in rat carotid arteries after endothelial denudation in absence of medial injury. (1990) Arteriosclerosis, 10, 1082-1087.
Grote, et al. Mechanical stretch enhances mRNA expression and proenzyme release of matrix metalloproteinase-2 (MMP-2) via nad(p)h oxidase-derived reactive oxygen species. Circulation Research. 2003;92(11): 80-6.
Linder, V. Mouse model of arterial injury. (1993) Circ. Res., 73, 792-796.
Manchio, J. Disruption of graft endothelium correlates with early failure after off-pump coronary artery bypass surgery. (2005) Ann. Thor. Surg. 79, 1991-1998.
Ramos, et al. Histologic fate and endothelial changes of distended and nondistended vein grafts. Ann Surg. 1976;183(3): 205-28.
Reneker, et al. Electrospinning of Nanofibers from Polymer Solutions and Melts. Adv Appl Mech 2007;41. doi:10.1016/S0065-2156(07)41002-X.
Sepehipour, A. Does a 'no-touch' technique result in better vein patency? (2011) Interact Cardiovasc Thorac Surg., 13, 626-630.

\* cited by examiner

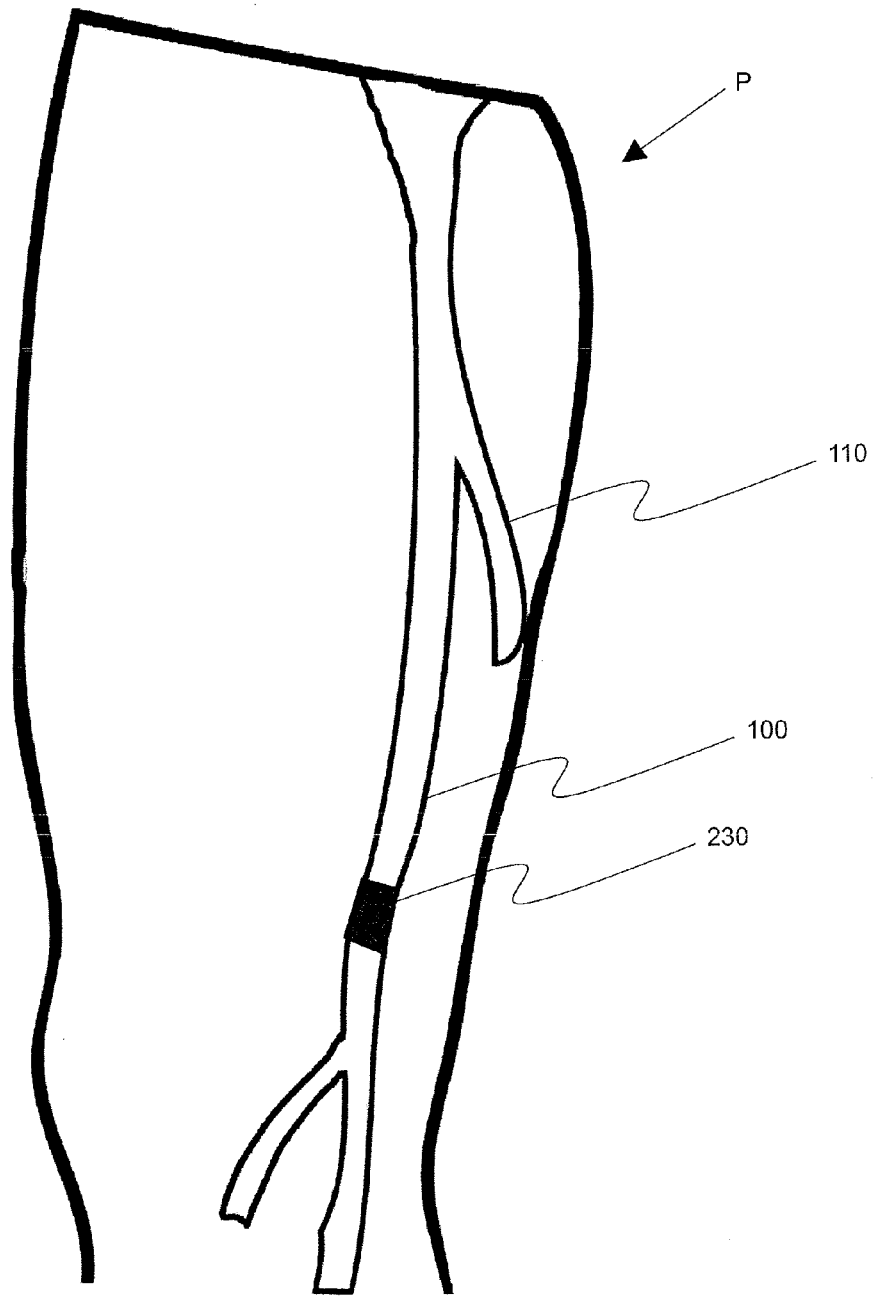

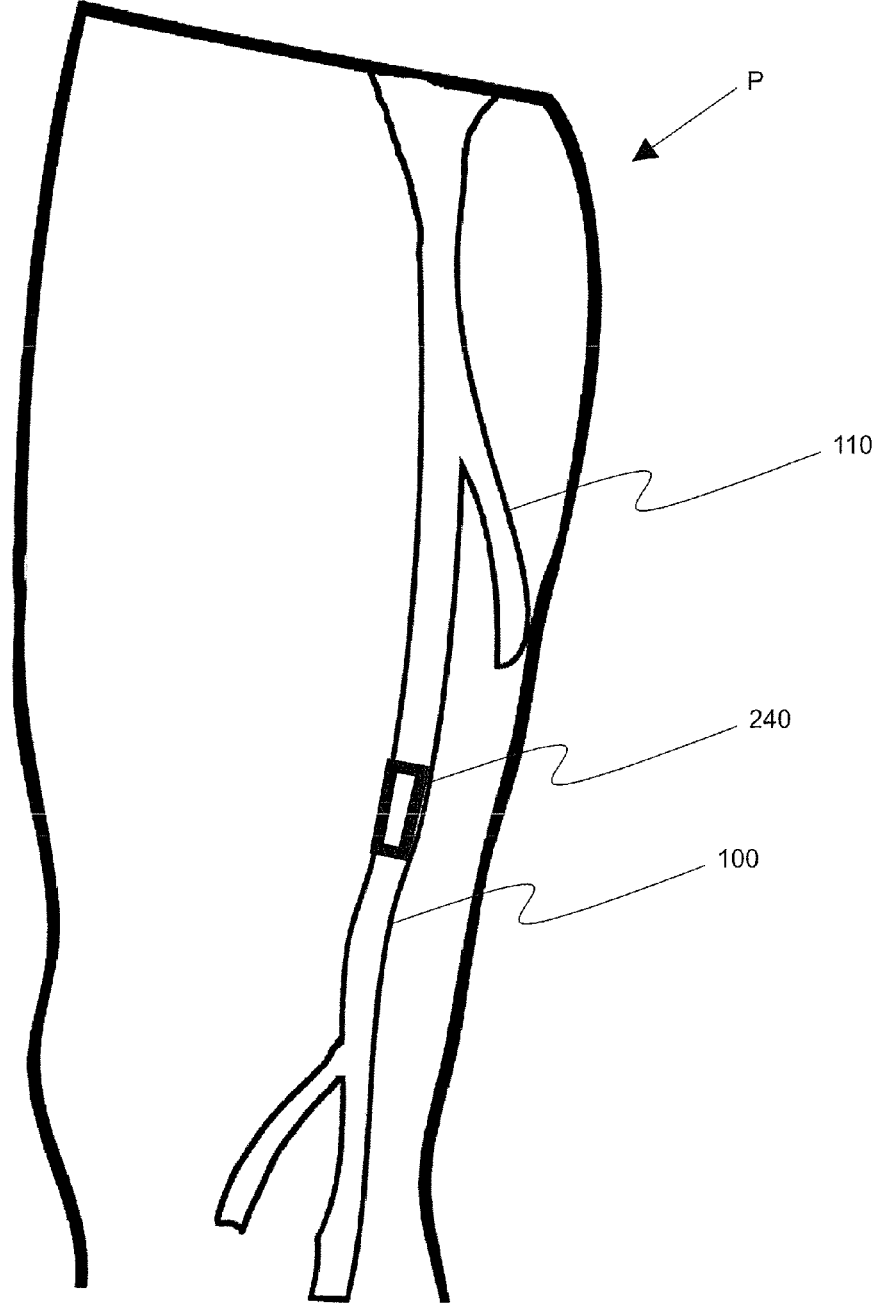

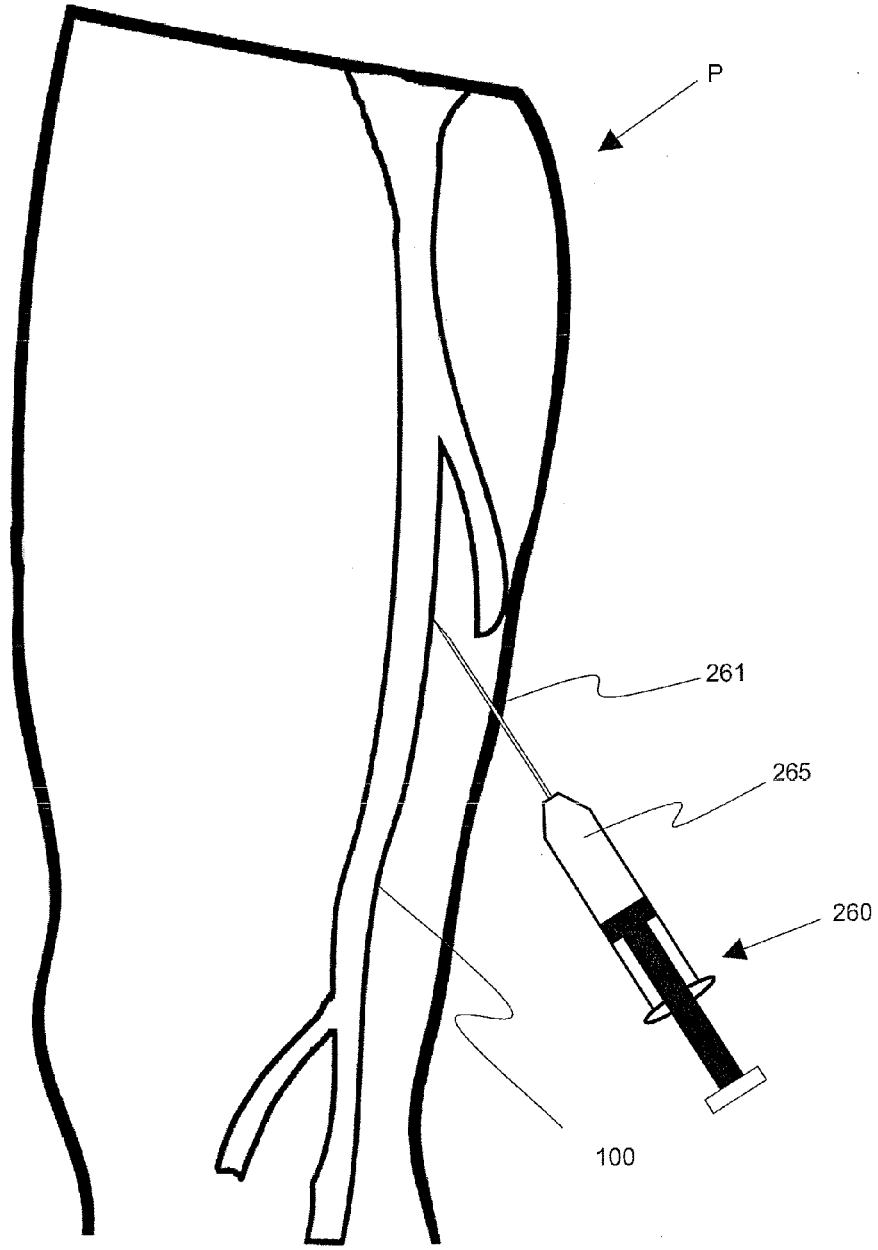

VESSEL REMODELING METHODS AND DEVICES FOR USE IN A GRAFT DEVICE

CROSS-REFERENCE TO RELATED APPLICATION

This application is a National Phase of International Application No. PCT/US12/47996 filed Jul. 24, 2012, which claims benefit of priority to U.S. Provisional Application No. 61/511,312 filed Jul. 25, 2011, the contents of which are hereby incorporated herein by reference in their entirety.

TECHNICAL FIELD

This application relates generally to methods and systems for creating graft devices for a mammalian patient, and more to particularly methods and devices for treating an in situ vessel, such as a vein for future use in a graft device.

BACKGROUND

Coronary artery disease, leading to myocardial infarction and ischemia, is a leading cause of morbidity and mortality worldwide. Current treatment alternatives consist of percutaneous transluminal angioplasty, stenting, and coronary artery bypass grafting (CABG). CABG can be carried out using either arterial or venous conduits and is the most effective and most widely used treatment to combat coronary arterial stenosis, with nearly 500,000 procedures being performed annually. In addition, there are approximately 80,000 lower extremity bypass surgeries performed annually. The venous conduit used for bypass procedures is most frequently the autogenous saphenous vein and remains the graft of choice for 95% of surgeons performing these bypass procedures. According to the American Heart Association, in 2004 there were 427,000 bypass procedures performed in 249,000 patients. The long term outcome of these procedures is limited due to occlusion of the graft vein or anastomotic site as a result of intimal hyperplasia (IH), which can occur over a timeframe of months to years.

Development of successful small diameter synthetic or tissue engineered vascular grafts has yet to be accomplished and use of arterial grafts (internal mammary, radial, or gastroepiploic arteries, for example) is limited by the short size, small diameter and availability of these vessels. Despite their wide use, failure of arterial vein grafts (AVGs) remains a major problem: 12% to 27% of AVGs become occluded in the first year with a subsequent annual occlusive rate of 2% to 4%. Patients with failed AVGs usually require clinical intervention such as an additional surgery.

IH accounts for 20% to 40% of all AVG failures within the first 5 years after CABG surgery. Several studies have determined that IH develops, to some extent, in all mature AVGs, and this is regarded by many as an unavoidable response of the vein to grafting. IH is characterized by phenotypic modulation, followed by de-adhesion and migration of medial and adventitial smooth muscle cells (SMCs) and myofibroblasts into the intima where they proliferate. In many cases, this response can lead to stenosis and diminished blood flow through the graft. It is thought that IH can be initiated by the abrupt exposure of the veins to the dynamic mechanical environment of the arterial circulation.

SUMMARY

For at least the above discussed reasons, and others, there is a need for devices and methods that provide enhanced AVGs and other improved grafts for mammalian patients. Desirably, the methods and devices will improve long term patency and minimize surgical and device complications.

In some aspects, a method of performing a medical procedure is provided. An in situ vessel is modified, such as by applying a force or pressure to or within the in situ vessel, or by implanting a device in or proximate to the in situ vessel. At least a segment of the in situ vessel is removed or harvested, typically weeks to months after the initiation of the vessel modification. The harvested segment is then implanted in the patient. In some embodiments, the harvested segment is fluidly connected to a source of oxygenated blood and an artery, such as at a location along the artery distal to an occlusion.

In some embodiments, the method includes selecting the vessel segment, such as a selection process including assessing an image of the patient. Vessel selection can be determined based on a number of factors including but not limited to: vessel availability; ease of access for harvesting; presence of sidebranches; vessel size; presence or absence of disease; degree of blockage of a vessel to be bypassed; patent age; a patient physiologic parameter; and an in situ vessel physiologic parameter. Numerous vessels can be selected for modification. In some embodiments, the vessel to be modified is selected from the group consisting of: vein; artery; urethra; intestine; esophagus; trachea; bronchi; ureter; duct; fallopian tube; and combinations of these.

The vessel to be modified can be a vein, such as a vein selected from the group consisting of: a saphenous vein; a femoral vein; a radial vein; an axillary vein; a cephalic vein; a basilic vein; and combinations of these. Alternatively or additionally, the vessel to be modified can be an artery, such as an artery selected from the group consisting of: an internal thoracic artery; a radial artery; a gastroepiploid artery; an inferior epigastric artery; a tibial artery; a dorsalis pedis artery; a brachial artery; a mesenteric artery; a femoral artery; and combinations of these. The time between initiating the vessel modification and harvesting the vessel can range from fifteen minutes to multiple months, such as at least six months. Vessel modification duration can be chosen to allow sufficient remodeling or other changes to the vessel that result from the modification. The modification itself can take place over time, such as a pressure increase over time or a drug delivered over a period of days to months.

The in situ vessel modification can comprise increasing the pressure within the vessel, such as to increase the pressure to a level of 50 mmHg or more, such as for a period of 2 weeks or more. The pressure increase can be varied, such as a continuous increase over time. The pressure increase can vary between values between 10 mmHg and 150 mmHg. The application of pressure can be steady or variable over time, such as a pulsatile pressure regimen. The pressure waveform can be of any shape and can be periodic or not.

The in situ vessel modification can be provided by a cuff placed around the thigh of the patient, such as to modify the pressure of an in situ vein, such as the saphenous vein. The cuff can include an inflatable bladder and a pump configured to continuously or intermittently inflate the bladder, such as inflations which occur at night while the patient is sleeping. The application of pressure can be steady or variable over time, such as a pulsatile pressure regimen. The pressure waveform can be of any shape and can be periodic or not.

The in situ vessel modification can be provided by a vacuum device, configured to apply a vacuum to the patient's skin proximate the vessel to be modified. The application of pressure can be steady or variable over time, such as a pulsatile pressure regimen. The pressure waveform can be of any shape and can be periodic or not.

The in situ vessel modification can be provided by an intravascular scaffold, such as a stent implanted within a saphenous vein and placed in a standard interventional catheter procedure. Alternatively or additionally, the in situ vessel modification can be provided by an extravascular scaffold, such as a restrictive coil placed around the external wall of the in situ vessel. The stent and/or extravascular scaffold can be permanent, removable after intended use, or biodegradable.

The in situ vessel modification can be provided by implanting a flow-limiting or flow occluding device proximate the in situ vessel, such as within the in situ vessel and/or within a sidebranch of the in situ vessel. The implant can be placed downstream and/or upstream to the segment to be harvested, such as when the vessel comprises a vein or an artery with flowing blood within. The implant can include a coating, such as a coating selected from the group consisting of: thrombotic agents; anti-thrombotic agents; anti-inflammatory agents; pro-inflammatory agents; cells such as stem cells; anti angiogenic agents; angiogenic agents; antifibrotic agents; fibrotic agents; cytostatic agents; antimitotic agents; pro-mitotic agents; other biological agents such as growth factors, cytokines, and antibodies; vasoactive agents; genetic transfection agents such as transfection factors, plasmids, and other gene vectors; and combinations of these.

The in situ vessel modification can be provided by ligating one or more sidebranches of the in situ vessel. Alternatively or additionally, a scar can be formed in or proximate to the in situ vessel. In some embodiments where the vessel is a vein, the modification can include modifying one or more venous valves, such as removal or disruption of the valves.

The in situ vessel modification can include delivering a drug or other agent within, into or proximate to the in situ vessel. The agent can be delivered by a bolus and/or a long-term infusion, such as a long-term continuous or intermittent infusion of an agent. Numerous agents can be used such as an agent selected from the group consisting of: thrombotic agents; anti-thrombotic agents; anti-inflammatory agents; pro-inflammatory agents; cells such as stem cells; anti angiogenic agents; angiogenic agents; antifibrotic agents; fibrotic agents; cytostatic agents; antimitotic agents; pro-mitotic agents; other biological agents such as growth factors, cytokines, and antibodies; vasoactive agents; genetic transfection agents such as transfection factors, plasmids, and other gene vectors; and combinations of these.

The in situ vessel modification can include bioelectrical stimulation so as to modify the vasoactivity status of the vessel, via smooth muscle, or the contraction state of the surrounding striated muscles. As a result, the vessel would be actively modified from within or passively modified by actively stimulating the surrounding tissues. Types of stimulation include: delivery of coherent and/or non-coherent light signals; irradiation with heat, ionizing and/or non-ionizing radiations.

The in situ vessel modification can include physical, mechanical, electrical or chemical stimulation, for example via a paracorporeal device. The stimulation can be delivery directly to the vessel or the surrounding areas of the vessels, for example via a local percutaneous access. The stimulation parameters can be controlled and adjusted based upon the desired vessel modification.

In some embodiments, the method further comprises applying a restrictive member about the vessel segment, such as a restrictive fiber matrix. The member can be bioerodible or configured to maintain its integrity over a long term implantation. The member can comprise a mechanical scaffold, such as a scaffold with a self-expanding or expandable stent structure.

In some embodiments, the method further comprises performing a diagnostic test, such as a test to assess vessel modification prior to the removal of one or more vessel segments. The diagnostic procedure can be used to modify one or more vessel modification parameters, such as to modify a pressure increase applied to the vessel. The diagnostic can be performed subsequent to a pre-determined remodeling period, such as to assess the remodeling and adjust one or more modification parameters in a closed-loop fashion. In some embodiments where the vessel is a vein, the diagnostic can be used to assess arterialization of the vein that has occurred due to the vessel modification procedure. Diagnostic tests can include but are not limited to: pressure measurement; stiffness measurement; compliance measurement; distensibility measurement; blood tests; pH measurement; temperature measurement; assessment of inflammation or inflammatory response; tissue impedance measurements; assessment of angiogenesis; and combinations of these. The diagnostic test can include an imaging procedure, such as an imaging procedure where an image is produced by one or more of: X-ray; fluoroscope; CT-scanner; ultrasound imaging device; and MRI.

In some aspects, a system for modifying an in situ vessel is provided. The system is constructed and arranged to modify a vessel prior to harvesting the vessel from a subject such as a mammalian being. The system can be configured to cause an increase in pressure within the in situ vessel. The system can comprise a cuff configured for placement around a thigh, such as to apply a positive pressure proximate to the in situ vessel. The system can be configured to apply a vacuum to the skin of the patient, such as to modify the pressure within the in situ vessel.

In some embodiments, the system includes an implant, such as an intravascular or extravascular scaffold constructed and arranged to modify the in situ vessel over time. The system can be configured to ligate one or more sidebranches of the in situ vessel. The system can be configured to create a scar in or proximate to the in situ vessel. The system can include a venous valve modifying device. The system can include an agent delivery device, such as an agent selected to modify the in situ vessel over time.

In some aspects, a method of performing an arterial bypass procedure is provided. A modification step is performed, modifying an in situ vein. Subsequently, a first portion of the in situ vein is fluidly attached to an oxygenated blood source, and a second portion of the in situ vein is fluidly attached to an artery.

In some embodiments, the artery is fully or partially occluded, and the first portion of the in situ vein is connected to a portion of the artery proximal to the occlusion. The second portion of the in situ vein is connected to a portion of the artery distal to the occlusion. Prior to the fluid attachments, the vessel can be harvested. Alternatively, the vessel is left in situ and connected to an occluded artery proximate the in situ vein.

BRIEF DESCRIPTION OF THE DRAWINGS

The accompanying drawings, which are incorporated in and constitute a part of this specification, illustrate various embodiments of the methods and systems described herein, and together with the description, serve to explain the principles of the invention. In the drawings:

FIG. 3C is a schematic view of an example intravascular occlusion device for treating a vessel to be harvested.

FIG. 3D is a schematic view of an example flow limiting device for treating a vessel to be harvested.

FIG. 5 is a schematic view of an example agent delivery device accessing a vessel to be harvested.

DETAILED DESCRIPTION OF THE DRAWINGS

Figure 1:
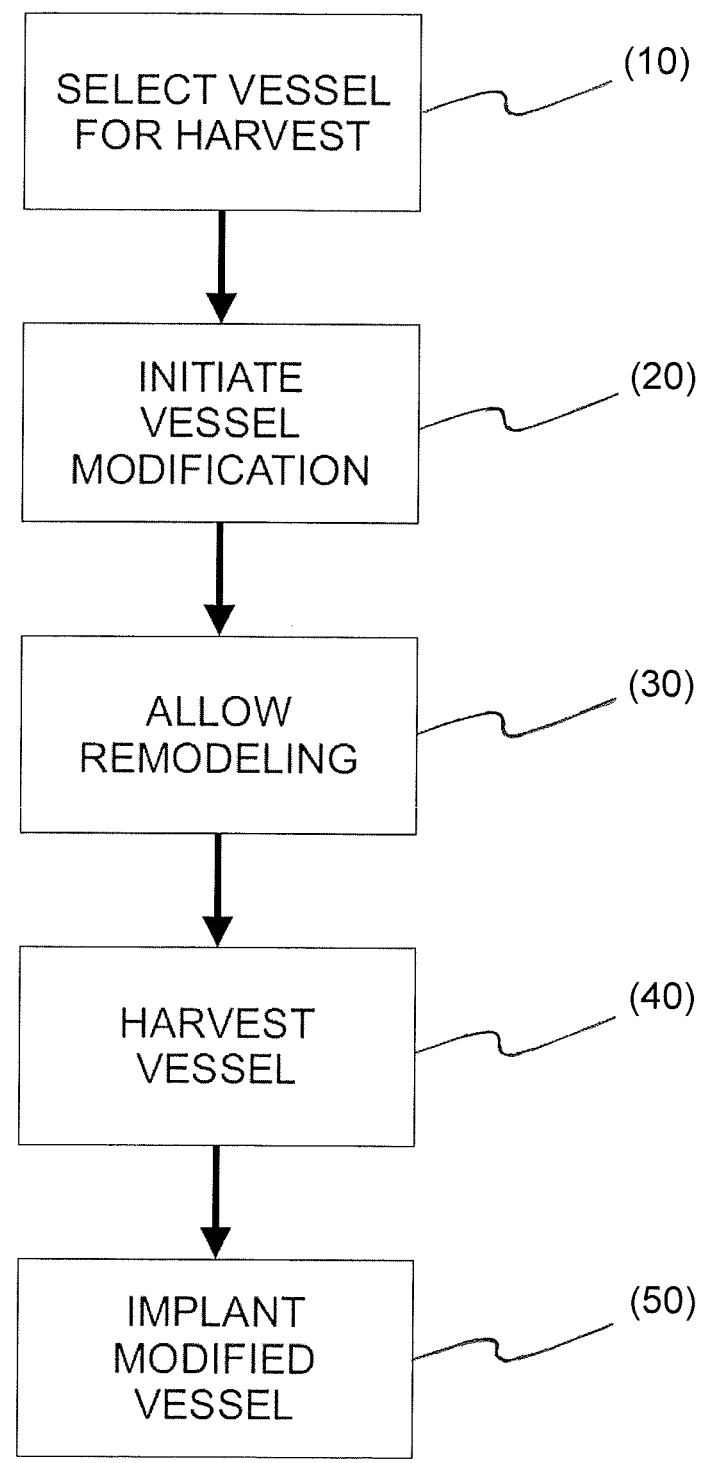
FIG. 1 is a flow chart depicting an example method of implanting a harvested vessel, including modifying the vessel prior to harvesting.

Reference will now be made in detail to the example embodiments of methods and systems described herein, examples of which are illustrated in the accompanying drawings. Wherever possible, the same reference numbers will be used throughout the drawings to refer to the same or like parts.

Provided herein is a method of modifying an in situ vessel, such as an in situ vein, prior to harvesting (i.e. explantation) for use in a patient treatment procedure. As used herein, "in situ vessel" refers to a native vessel that is modified or otherwise treated in situ. Also used herein, "modification" of a native vessel can include treating a physical or chemical parameter causing the vessel to modify itself via remodeling; modifying a geometric parameter such as by restricting or ligating side branches; and combinations of these.

Segments of harvested veins and other tubular tissue conduits are often used in clinical procedures to support the flow of blood or other body fluid. In some embodiments, the modified in situ vessel is a vein located in a limb of a patient, such as a saphenous vein located in the leg of a patient. The modified saphenous vein is harvested and fluidly connected to a source of oxygenated blood to bypass one or more coronary arteries.

The vessel modifications described herein can be used to create a graft device for implantation in a patient that has improved clinical outcomes as compared to implantation of unmodified harvested vessels. The modification can be performed and/or initiated the same day as the implantation procedure, or days, weeks or months ahead of the implantation. The modification can be configured to allow the in situ vessel to remodel or otherwise change over time, prior to harvesting, such as a modification that occurs over weeks to months. After sufficient remodeling or other modifications have occurred, the vessel can be harvested and then implanted in the patient, typically during the same day in a single setting, such as an operating room, catheter lab or other clinical setting.

In some embodiments, one or more structures or coverings can be applied to the harvested, modified vessel prior to implantation. In some embodiments, a fiber matrix is circumferentially applied about the exterior surface of the modified harvested vessel. This fiber matrix can be applied using an electrospinning process, such as that described in applicants co-pending International Patent Application Serial Number PCT/US2012/21209, filed on Jan. 13, 2012, and entitled "Apparatus for Creating Graft Devices," the contents of which are hereby incorporated herein by reference in their entirety. Other coverings can be placed about the circumference of the modified, harvested vessel, such as a mechanical scaffold (e.g. a stent) as is described in U.S. Pat. No. 8,057,537, issued on Nov. 15, 2011, entitled "Compliant Venous Graft," the contents of which are hereby incorporated herein by reference in their entirety.

Alternative vessel coverings can be applied such as those described in applicants co-pending U.S. patent application Ser. No. 13/515,996, filed Jun. 14, 2012, entitled "Graft Devices and Methods for Use" the contents of which are hereby incorporated herein by reference in their entirety. In some embodiments, one or more pre-made fibers, typically supplied on spools, are wrapped around the modified vessel. In some embodiments, a liquid covering, such as a liquid polymer (a polymer solution, a polymer suspension, or a polymer melt) or other liquid material, can be applied to the modified vessel in liquid (non-fibrous) form, which then solidifies or partially solidifies over time. The modified vessel can be dipped into the liquid material, or the liquid material can be applied to the modified vessel with a tool, such as a brush or a spraying device.

Typical polymers used to cover the harvested, modified vessels include natural polymers, synthetic polymers, and blends of natural and synthetic polymers. Polymers can be either biodegradable, non-biodegradable, or include both biodegradable and non-biodegradable materials. For example and without limitation, natural polymers include silk, chitosan, collagen, elastin, alginate, cellulose, polyalkanoates, hyaluronic acid, or gelatin. Natural polymers can be obtained from natural sources or can be prepared by synthetic methods (including by recombinant methods) in their use in the context of the invention described herein. Non-limiting examples of synthetic polymers include: homopolymers, heteropolymers, co-polymers and block polymers or co-polymers.

Typical coverings are substantially or essentially contiguous about an internal or external wall of the harvested, modified vessel, meaning that the covering forms a continuous, supportive tube on a surface and about a circumference of a portion, but not necessarily over the entire surface (e.g., length) of the modified vessel. The covering can be "restrictive", meaning that the covering is in substantial contact with the outer surface of the harvested vessel, or the covering can be narrowly spaced and proximate to the outer surface of the modified vessel (e.g. to restrict after an initial unrestricted expansion). The covering can also be "constrictive", meaning that the diameter of the modified vessel is reduced by the application of the covering. Restrictive coverings can be used to reinforce, restrict, hinder and/or prevent substantial circumferential expansion of the modified vessel, such as when used as a bypass graft and is exposed to arterial pressure; or otherwise when the modified vessel is radially expanded. The degree of restriction by the covering typically is such that when exposed to internal pressure, such as typical arterial pressures, the modified vessel is prevented from distending to the extent that would occur without such restriction. Constrictive coverings can be used to match the internal diameter of the modified vessel to the internal diameter of the target tissue (e.g. artery) being connected by the modified vessel. For example, quite often a vein being used as a coronary artery bypass graft has a considerably larger internal diameter than the target coronary artery being bypassed. In order to reduce flow disturbances, it is advantageous to match the internal diameter of the graft (harvested, modified vessel) to the internal diameter of the stenosed coronary artery. The covering can be durable or temporary, such as when the restrictive nature of a biodegradable covering can decline over time. The covering can have a relatively uniform cross section, or a cross section that varies along the length of the covering.

Coverings can be constructed and arranged in a manner specific to a patient morphological or functional parameter. These parameters can be selected from the group consisting of: vessel size such as diameter, length, and/or wall thickness; taper or other geometric property of a harvested vessel or vessel intended for anastomotic attachment; size and location of one or more sidebranch ostium or antrum within the harvested vessel; patient age or sex; vessel elasticity or compliance; vessel vasculitis; vessel impedance; specific genetic factor or trait; and combinations of these.

As used herein, the term "polymer composition" is a composition comprising one or more polymers. As a class, "polymers" includes homopolymers, heteropolymers, co-polymers, block polymers, block co-polymers and can be both natural and synthetic. Homopolymers contain one type of building block, or monomer, whereas co-polymers contain more than one type of monomer. For example and without limitation, polymers comprising monomers derived from alpha-hydroxy acids including polylactide, poly(lactide-co-glycolide), poly(L-lactide-co-caprolactone), polyglycolic acid, poly(dl-lactide-co-glycolide), poly(l-lactide-co-dl-lactide); monomers derived from esters including polyhydroxybutyrate, polyhydroxyvalerate, polydioxanone and polygalactin; monomers derived from lactones including polycaprolactone; monomers derived from carbonates including polycarbonate, polyglyconate, poly(glycolide-co-trimethylene carbonate), poly(glycolide-co-trimethylene carbonate-co-dioxanone); monomers joined through urethane linkages, including polyurethane, poly(ester urethane) urea elastomer.

A biodegradable polymer is "biocompatible" in that the polymer and degradation products thereof are substantially non-toxic, including non-carcinogenic non-immunogenic and non-sensitizing, and are cleared or otherwise degraded in a biological system, such as an organism (patient) without substantial toxic effect. Non-limiting examples of degradation mechanisms within a biological system include chemical reactions, hydrolysis reactions, and enzymatic cleavage. Biodegradable polymers include natural polymers, synthetic polymers, and blends of natural and synthetic polymers. For example and without limitation, natural polymers include silk, fibrin, chitosan, collagen, elastin, alginate, cellulose, polyalkanoates, hyaluronic acid, or gelatin. Natural polymers can be obtained from natural sources or can be prepared by synthetic methods (including by recombinant methods) in their use in the context of the invention described herein. Non-limiting examples of synthetic polymers include: homopolymers, heteropolymers, co-polymers and block polymers or co-polymers.

As used herein, the terms "comprising," "comprise" or "comprised," and variations thereof, are meant to be open ended. The terms "a" and "an" are intended to refer to one or more.

Grammatical conjunctions are intended to express any and all disjunctive and conjunctive combinations of conjoined clauses, sentences, words, and the like, unless otherwise stated or clear from the context. For example, the phrase "at least one of A, B, and C" can include at least one of A, at least one of B, and at least one of C; or can include at least one of A, at least one of B, or at least one of C; or can include only A, only B, only C, or any combination of A, B and C, where A, B, and C can be a clause, sentence or a word.

As used herein, the term "patient" or "subject" refers to members of the animal kingdom including but not limited to human beings.

As used herein, a "fiber" comprises an elongated, slender, thread-like and/or filamentous structure.

As used herein, a "matrix" is any two- or three-dimensional arrangement of elements (e.g., fibers), either ordered (e.g., in a woven or non-woven mesh) or randomly-arranged (as is typical with a mat of fibers typically produced by electrospinning).

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain terminal groups are incorporated into the polymer backbone. A polymer is said to comprise a specific type of linkage if that linkage is present in the polymer.

FIG. 1 illustrates a flow chart depicting an example method of creating a graft device for use in a medical procedure, for example an occluded artery bypass procedure. The method typically includes selecting an in situ vessel of a living being; modifying the vessel in situ (i.e. in its natural location prior to harvesting); harvesting the vessel; and implanting the vessel in a patient, such as to make a fluid connection between two body locations. In some embodiments, the vessel is a vein and implantation of the modified vein includes attaching one end to a source of oxygenated blood and the opposite end to a portion of an occluded artery, downstream from the occlusion. The harvested vein can have been further modified, such as by adding a covering, such as to create a covered graft device described herein, for example a covered graft device described in further detail below in reference to FIG. 9.

First, a vessel of a living being can be selected for harvest. (10) Typically, the living being is the patient that will receive the vessel after modification and harvesting from the in situ site. Alternatively, the patient can be a second living being with physiologic characteristics suitable to receive the harvested, modified vessel from the first living being. The vessel is typically selected from the group consisting of: vein; artery; urethra; intestine; esophagus; trachea; bronchi; ureter; duct; fallopian tube and combinations of these. In some embodiments, the vessel is a vein, such as a vein selected from the group consisting of: a saphenous vein; a femoral vein; a radial vein; an axillary vein; a cephalic vein; a basilic vein; and combinations of these. In some embodiments, the vessel to be modified and harvested is an artery, such as an artery selected from the group consisting of: an internal thoracic artery; a radial artery; an gastroepiploid artery; an inferior epigastric artery; a tibial artery; a dorsalis pedis artery; a brachial artery; a mesenteric artery; a femoral artery; and combinations of these. A particular portion or segment location of the vessel to be harvested can also be selected at this time. Vessel and vessel segment selection can involve the use of one or more imaging devices, such as an X-ray, a fluoroscope, a CT scanner, an ultrasound imager or an MRI. Vessel segments to be modified and subsequently harvested are chosen based on a number of factors, including but not limited to: vessel availability; ease of access for harvesting; presence of sidebranches; vessel size; presence or absence of disease; degree of blockage of a vessel to be bypassed (if applicable); patent age; and other patient and vessel physiologic parameters. For coronary artery bypass procedures, vessels such as saphenous veins are typically chosen and harvested from the patient's leg in a standard vessel harvesting surgical procedure.

Next, the selected vessel can be modified in situ, in other words, without detachment or explantation from its natural site. (20) The modification step can be performed using various devices and methods, a number of which are described below. The modification can be performed to improve the harvesting, the clinical procedure in which the vessel is implanted, and/or the outcomes of the entire patient treatment. Typically, the harvested vessel is a flow conduit, and the in situ vessel modification is performed to improve the long term patency of the implanted, modified vessel.

Typical vessel modifications include but are not limited to: implanting a device within or around the vessel; continuously or intermittently increasing blood or other pressure within the vessel; ligating sidebranches of the vessel; creating scar tissue in the walls of the vessel; disrupting, removing or otherwise modifying valves such as venous valves within the vessel; delivering an agent (e.g. a drug, a cell or other agent) into, within the walls of, or exterior but proximate to the in situ vessel; and combinations of these. Each of these modifications is described in detail with reference to the figures herein. Modification of the in situ vessel (20) can be performed in multiple steps, at various times and durations.

In some embodiments, the vessel to be modified and harvested can be a saphenous vein, in either or both legs of a patient, and a modification includes elevating the pressure within and/or around the in situ saphenous vein or veins prior to harvesting. Generally, normal pressure in the in situ saphenous vein, i.e. pressure prior to a vein modification, is low (e.g., very low), typically between 3 and 80 mmHg depending on patient position. Elevated pressures, i.e. pressure subsequent to a vein modification, can be caused to approximate the patient's current arterial blood pressure (e.g. approximately 120 over 80 mmHg in a healthy patient), or higher. The elevated pressure can be maintained continuously or intermittently. In some embodiments, the pressure can be elevated such that the pressure is elevated for a first period of time to a first elevated pressure level, followed by elevating the pressure to a second elevated pressure level for a second period of time. This process can be repeated one or more times, such as in multiple increments, to achieve the desired result, and can include one or more time periods where the vessel pressure is not elevated. In some embodiments, the pressure can be elevated to a pressure of approximately 50 mmHg for a period of about two weeks. In some embodiments, the pressure can be elevated to a pressure of approximately 80 mmHg for a period of about two weeks. In some embodiments, the pressure can be elevated to a pressure of approximately 100 mmHg for a period of about two weeks. In some embodiments, the pressure can be elevated incrementally between approximately 20 mmHg and 100 mmHg, such as over a period of twelve weeks in increments of about 7.25 mmHg per week. In some embodiments, the pressure can be elevated between approximately 20 mmHg and 150 mmHg, such as over a period of 12 weeks in increments of about 11.75 mmHg per week. In some embodiments, the pressure can be elevated between approximately 20 mmHg and 100 mmHg, such as over a 16 week period in increments of about 5.3 mmHg per week. In some embodiments, the pressure can be elevated between approximately 10 mmHg and 150 mmHg, such as over a 16 week period in increments of about 8.7 mmHg per week. In some embodiments, the pressure can be elevated between 10 mmHg and 100 mmHg, such as over a 2 week period in increments of about 6.2 mmHg per day. In some embodiments, the pressure can be elevated between 10 mmHg and 150 mmHg, such as over a 2 week period in increments of about 10 mmHg per day. During the exposure to the elevated pressure, or intermittently elevated pressure, remodeling of the vessel (e.g. vein) wall will occur. These modifications will be beneficial when a harvested, modified venous segmented is implanted in an arterial bypass procedure after which the vein segment will be exposed to the patient's arterial pressures.

In some embodiments, the in situ vessel modification can include bioelectrical stimulation so as to modify the vasoactivity status of the vessel, via smooth muscle, or the contraction state of the surrounding striated muscles. As a result, the vessel would be actively modified from within or passively modified by actively stimulating the surrounding tissues. Types of stimulation include: delivery of coherent and/or non-coherent light signals; irradiation with heat, ionizing and/or non-ionizing radiations.

In some embodiments, the in situ vessel modification can include physical, mechanical, electrical or chemical stimulation, for example via a paracorporeal device. The stimulation can be delivery directly to the vessel or the surrounding areas of the vessels, for example via a local percutaneous access. The stimulation parameters can be controlled and adjusted based upon the desired vessel modification.

The type of modification to the in situ vessel can be selected or adjusted based on a patient morphological or functional parameter. (20) These patient parameters can be selected from the group consisting of: vein size such as diameter, length, and/or wall thickness; taper or other geometric property of a selected vein or vein intended for anastomotic attachment; size and location of one or more sidebranch ostium or antrum within the selected vein; patient age or sex; vein elasticity or compliance; vein vasculitis; vein impedance; specific genetic factor or trait; and combinations of these.

An optional step can be performed in which the vessel is allowed to be modified while undergoing a remodeling period. (30) Remodeling periods can consist of minutes to days, or weeks to months. Various modification methods and devices can benefit from prolonged exposure to the modification in the remodeling period. In some embodiments, elevated pressure, continuous or intermittent, can be provided for weeks to months to allow a vein segment to assume arterial properties. In some embodiments, a vessel segment is exposed to a drug, cells and/or other agents, acutely or continuously, and remodeling occurs over time. In some embodiments, one or more sidebranches are ligated or occluded, or one or more implants are placed in or around the vessel segment to be harvested and the remodeling that occurs over time periods such as weeks to months improves the clinical outcomes achieved when the vessel segment is eventually harvested and implanted in a patient as a medical treatment.

The vessel can then be harvested. (40) Vessel harvesting can be performed via any means as known to those skilled in the art, typically a surgical or minimally invasive surgical procedure involving severing a vessel segment with a cutting device and ligating (e.g. with clips) the newly exposed ends of the remaining vessel portions. In some embodiments, the segment of vessel to be harvested is determined when the vessel for harvest is selected (10). The vessel segment selection can be performed using an imaging device, such as an X-ray, a fluoroscope, a CT scanner, an ultrasound imager or an MRI.

Subsequent to harvesting the vessel (e.g., vein), the vein can undergo various treatments or other modifications. For example, a covering such as a fiber matrix can be applied via an electrospinning procedure resulting in a covered bypass graft. Alternatively or additionally, spiral or other wrapped coverings, dipped coverings, mechanical scaffold coverings and other modifications can be performed upon the harvested, modified vessel, prior to implantation.

The modified vessel (e.g., a graft device comprising the modified vessel) can then be implanted in the patient. (50) Typically, the graft device can be implanted during a bypass procedure in which one end of a modified vein is attached to a source of arterial blood, and the other end is attached to an occluded artery at a location distal to the occlusion.

In some embodiments, the method steps indicated by (10), (20), (30), (40), and/or (50) occur during a single clinical procedure. In such embodiments, initiate vessel modification (20) can be performed at least 15 minutes prior to harvesting the vessel (40). In some embodiments, the vessel is a vein that is modified at least 15 minutes prior to harvesting and less than four hours prior to harvesting. In some embodiments, the vein is modified at least 15 minutes prior to harvesting and less than two hours prior to harvesting. In some embodiments, the vein is modified at least 15 minutes prior to harvesting and less than one hour prior to harvesting. In some embodiments, the vein is modified at least 15 minutes prior to harvesting and less than 30 minutes prior to harvesting.

Alternatively, modification of the vessel (20) and harvesting of the vessel (40) occur during two or more separate clinical procedures. For example, a first clinical procedure can be performed to modify a vein in situ, and a second clinical procedure can be performed to harvest the vein. The time lapse between the two procedures can range from at least eight hours to at least six months, for example, one week; one month; or three months. In some embodiments, implanting the harvested, modified vessel (50) can occur during the second clinical procedure. Alternatively, implanting the harvested, modified vessel (50) can occur during a third clinical procedure.

In some example methods, a vein is selected and modified in situ and used in a bypass procedure, however the vein is not harvested, i.e., the method step depicted at (40) of FIG. 1 is not included in the procedure, and the method step depicted at (50) of FIG. 1 includes fluidly connecting the in situ vein proximally and distally to an in situ occluded artery. In some of such methods, a vein, such as a cardiac vein, can be used to bypass a neighboring artery, such as a neighboring coronary artery, as is described in detail in reference to U.S. patent Ser. No. 08/730,327, filed Oct. 11, 1996 and entitled "Methods and Apparatus for Bypassing Arterial Obstructions and/or Performing Other Transvascular Procedures", the contents of which are hereby incorporated herein by reference in their entirety. In some embodiments, the vein is the anterior intraventricular vein (AIV), and the bypassed artery is the left anterior descending artery (LAD).

Figure 2A:
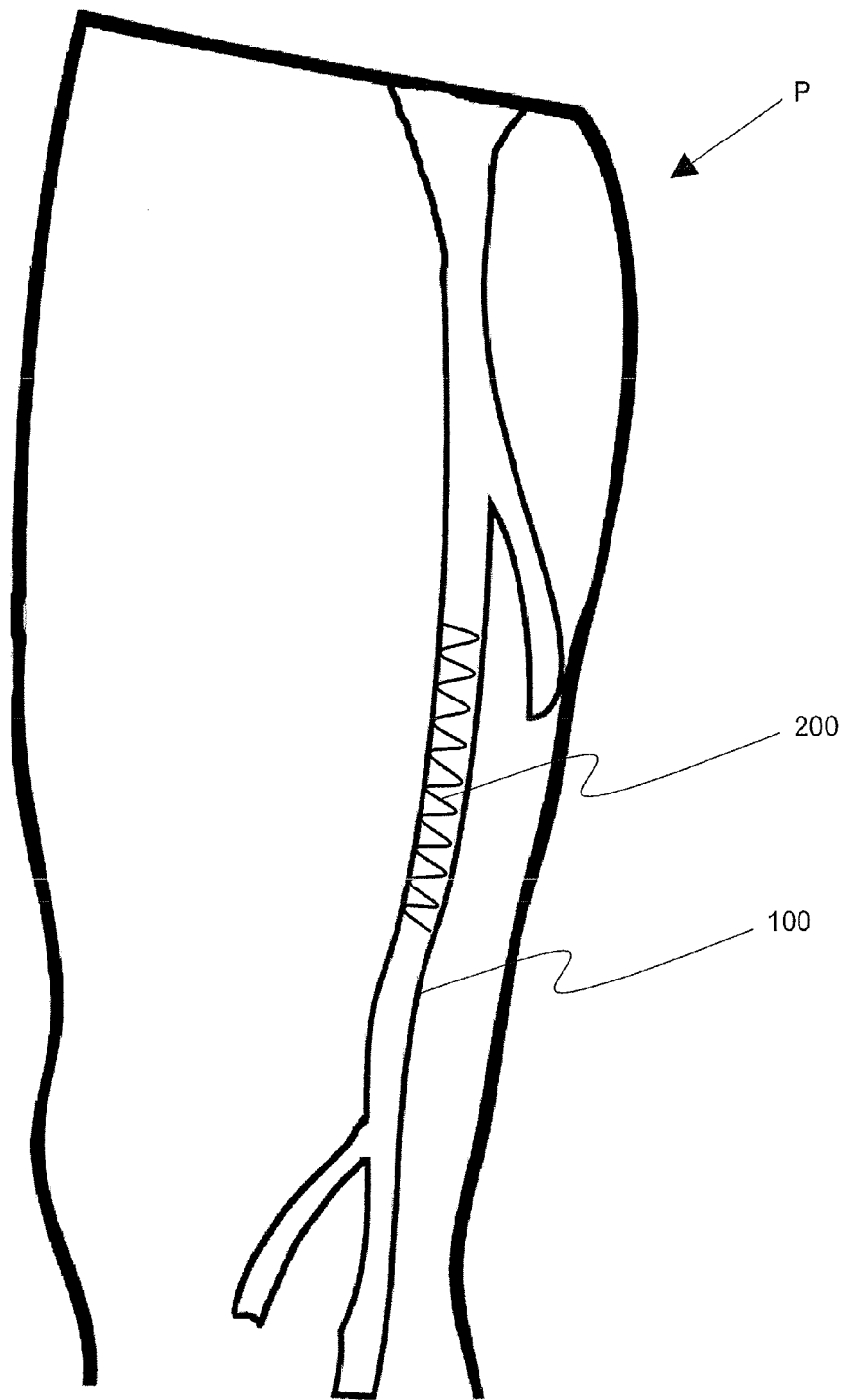
FIG. 2A is a schematic view of an example intravascular scaffold for pre-treating a vessel to be harvested.
Figure 2B:
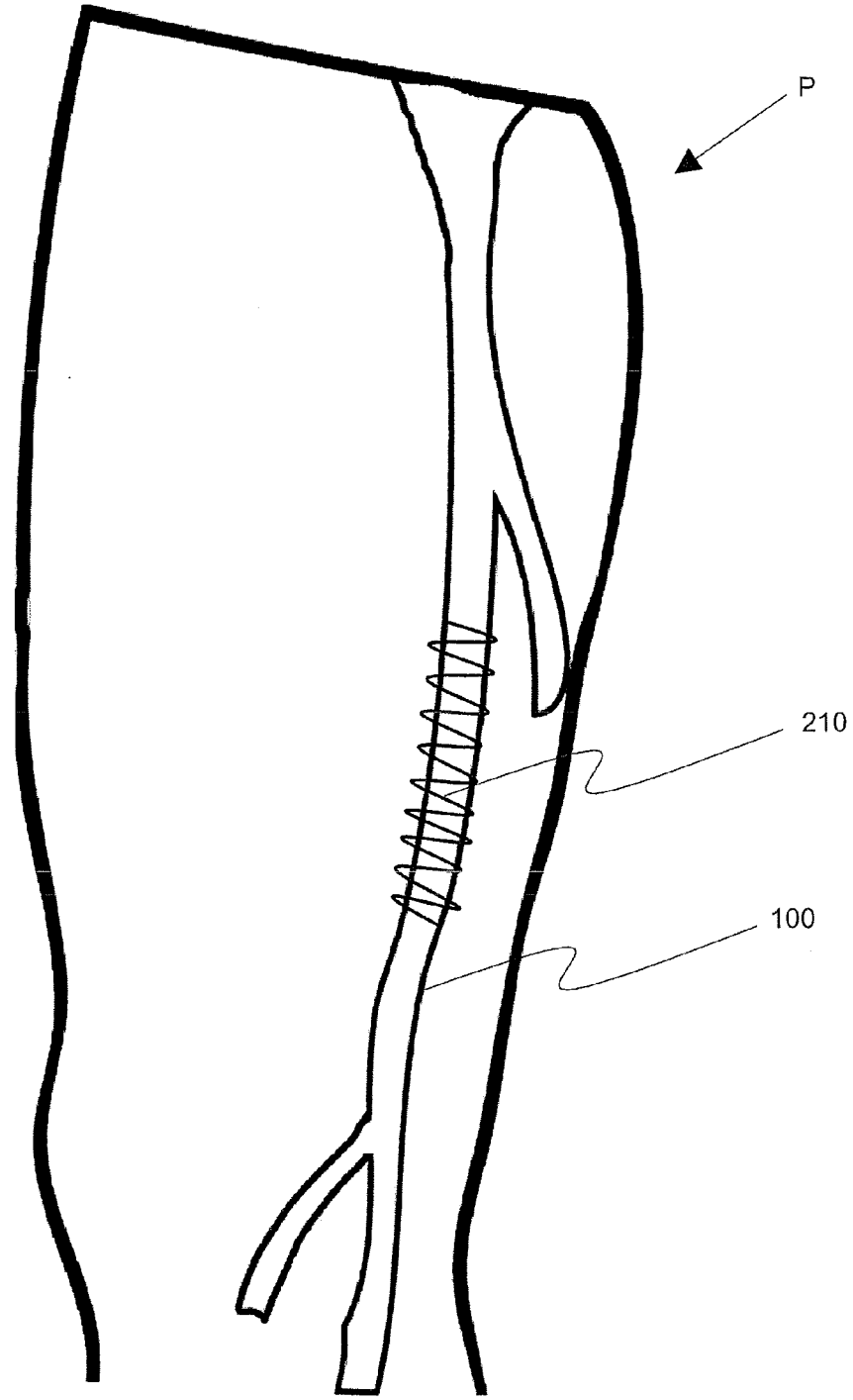
FIG. 2B is a schematic view of an example extravascular scaffold for pre-treating a vessel to be harvested.

FIGS. 2A and 2B illustrate an example in situ vein modification via implantation of a mechanical scaffold within and around, respectively, an in situ vein of the patient's leg, typically a saphenous vein. Referring specifically to FIG. 2A, a mechanical scaffold, stent 200 can be implanted within in situ vein 100 of patient P. Stent 200 can comprise a standard balloon expandable or self-expanding metallic or other biocompatible material structure, similar to those used in stenting occluded coronary arteries. Stent 200 can be implanted in a standard interventional procedure, such as an over-the-wire procedure including a balloon deployment catheter. Implantation of stent 200 can cause a modification in vein 100 that occurs over time. The biological response to foreign materials within the vein, such as stent 200, is similar to those that occur to such materials when placed within arteries. An inflammatory reaction, stimulated within the surrounding tissue and by the surrounding blood can occur and result in recruitment of inflammatory cells to the area adjacent the stent 200. These cells consist chiefly of macrophages and neutrophils that present in the period between the implant time to approximately days after the initial implant and are followed by the appearance of smooth muscle cells and fibroblasts within the tissue that begin to increase the bulk and strength of the surrounding tissue. The vessel benefits from increased bulk in a number of ways. Much of the proliferative tissue can contribute additional strength to the vein to resist overdilation, such as after being exposed to arterial pressure. Also, the lumen of the vessel can be somewhat decreased as a result of the increased tissue, causing the hoop stress that develops from internal pressure to be decreased and thus vessel dilation due to increased pressure will be reduced.

Referring specifically to FIG. 2B, a stent 210 can be implanted around in situ vein 100 of patient P. Stent 210 can be implanted in a surgical or minimally invasive surgical procedure that includes "cutting down" and potential dissection of a portion of vein 100 away from neighboring tissue. Stent 210 can be a coiled filament which is meticulously rotated such as to surround the outer wall of vein 100, or can comprise a sheet of material which is wrapped around vein 100. Similar to stent 200 above, stent 210 can cause a modification in vein 100 that occurs over time. The biological response to foreign materials surrounding the vein, such as stent 210, can be similar to those that occur to such materials when placed within connective tissue in other sites of the patient. An inflammatory reaction is stimulated within the surrounding tissue and results in recruitment of inflammatory cells to the area adjacent stent 210. These cells consist chiefly of macrophages and neutrophils that present within days of implantation. The inflammatory cells are followed by the appearance of smooth muscle cells and fibroblasts within the tissue. Those cells that proliferate within the vein begin to increase the bulk and strength of the surrounding tissue. The vessel benefits from increased bulk in a number of ways. Much of the proliferative tissue can contribute additional strength to the vein to resist overdilation, such as after being exposed to arterial pressure. Also, the lumen of the vessel can be somewhat decreased as a result of the increased tissue, causing the hoop stress that develops from internal pressure to be decreased and thus vessel dilation due to increased pressure will be reduced. Furthermore, the tissue surrounding the implant will eventually produce a fibrous barrier around the implant that will contract to form a barrier between the implant and the surrounding tissue. This barrier will contribute some strength to the vein to assist it in resisting overdilation when exposed to elevated pressure.

While FIGS. 2A and 2B illustrate stent-like structures implanted within and around, respectively, an in situ vein, such structures can be implanted in or around other vessels of a living body. The eventually harvested segment of vessel 100, typically including stent 200 or stent 210, can be implanted in patient P or another patient. Stent 200 or stent 210 can be removed prior to implantation or left in place.

Figure 3A:
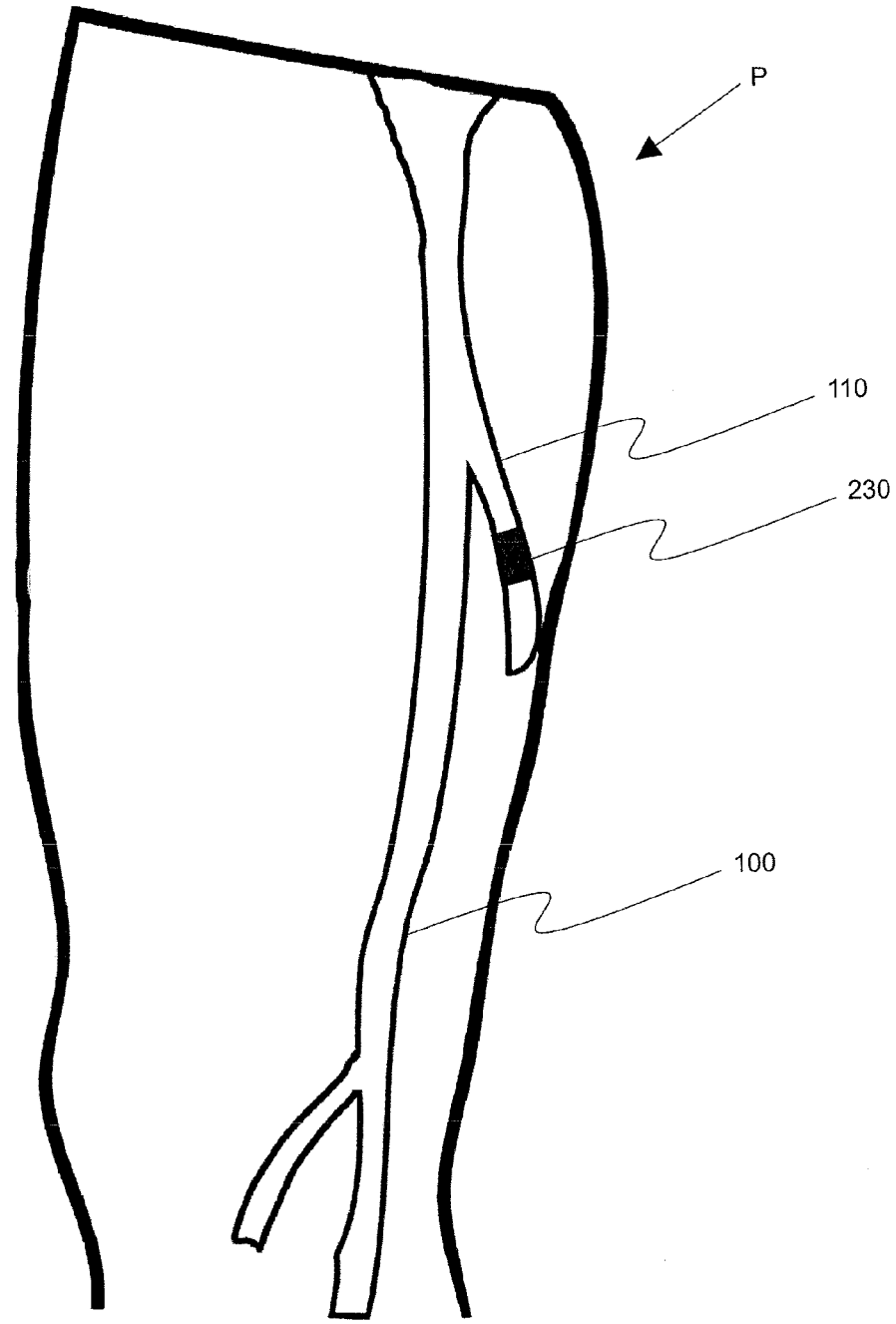
FIG. 3A is a schematic view of an example intravascular occlusion device for treating a sidebranch of a vessel to be harvested.
Figure 3B:
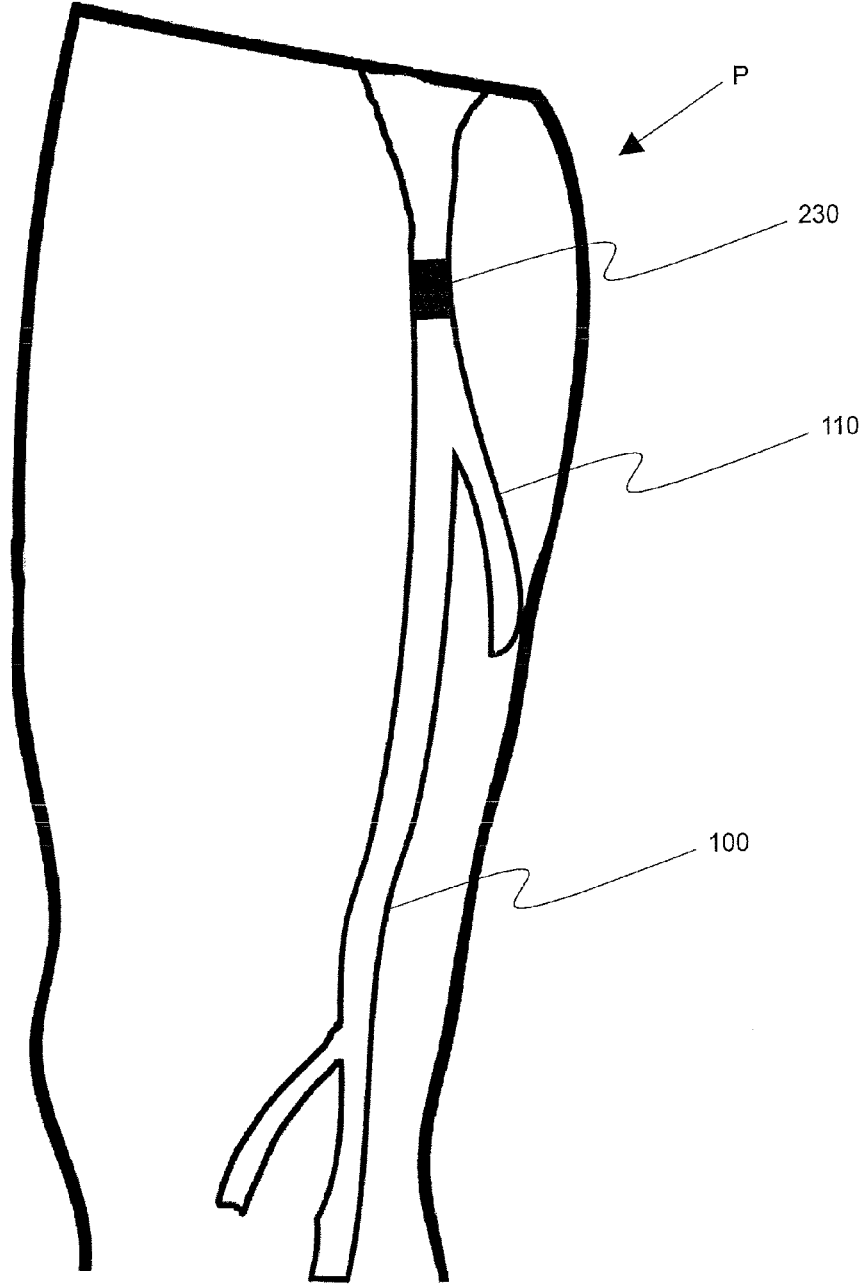
FIG. 3B is a schematic view of an example intravascular occlusion device for treating a vessel to be harvested.

FIGS. 3A-D illustrate various embodiments of an in situ vessel modification via implantation of a flow modifying device within the in situ vessel. For example, referring specifically to FIG. 3A, a flow occluding device (e.g., blocker) 230 can be placed within a sidebranch 110 of vein 100, typically a saphenous vein, at a location proximate to vein 100. In FIG. 3B, blocker 230 is placed distal to or in a distal portion of vein 100, and in FIG. 3C, blocker 230 is placed proximal to or in a proximal portion of vein 100. With specific reference to veins in the limbs of a patient, blood flows toward the heart from a proximal portion to a distal portion, thus the proximal portion of vein 100 is closer to patient P's feet, while the distal portion of vein 100 is closer to patient P's heart. In FIG. 3D, a flow reducing device (e.g., flow limiter) 240 partially obstructs and thus resists blood flow through vein 100. Similar to blocker 230, flow limiter 240 can be positioned distal to or in a distal portion of vein 100 and can be positioned proximal to or in a proximal portion of vein 100. In some embodiments, blocker 230 and/or flow limiter 240 can include embolization coils, such as those sold by Target Therapeutics, of Fremont, Calif. In some embodiments, blocker 230 and/or flow limiter 240 can include an end covered stent. In addition, blocker 230 and/or flow limiter 240 can be coated such as with a thrombogenic coating that causes blood to clot proximate to blocker 230 and/or flow limiter 240. Blocker 230 and flow limiter 240 can include one or more coatings including one or more agents which are released acutely or over time, and configured to modify vein 100. Typical agents include but are not limited to: thrombotic agents; anti-thrombotic agents; anti-inflammatory agents; pro-inflammatory agents; cells such as stem cells; anti angiogenic agents; angiogenic agents; anti-fibrotic agents; fibrotic agents; cytostatic agents; antimitotic agents; pro-mitotic agents; other biological agents such as growth factors, cytokines, and antibodies; vasoactive agents; genetic transfection agents such as transfection factors, plasmids, and other gene vectors; and combinations of these.

Combinations of flow occluding and flow restricting devices, such as blocker 230 and flow limiter 240 respectively, can be placed in various locations within the lumen of vein 100, distal or proximal to vein 100, and/or within one or more sidebranches of vein 100, such as to cause vein 100 to remodel over time. Blocker 230 and flow limiter 240 can be used to modify the pressure present in vein 100, modify flow direction; modify flow characteristics such as turbulence, cause a physiologic reaction to an implant; cause other physiologic responses; and combinations of these.

Alternative to blocker 230, a segment of vessel 100 or a sidebranch, such as sidebranch 110, can be occluded with a device configured to apply an external force to the walls of vein 100, not shown, but typically a ligation clip or suture surrounding or partially surrounding a segment of vein 100. In some embodiments, ligation of at least one sidebranch in the modification step avoids the need to ligate that sidebranch after the harvesting procedure. In some embodiments, at least two sidebranches can be ligated. Ligated sidebranches are typically along the segment of vein 100 to be removed. Alternatively or additionally, ligated sidebranches can be superior and/or inferior to the segment of vein 100 to be removed.

Figures 4A, 4B:
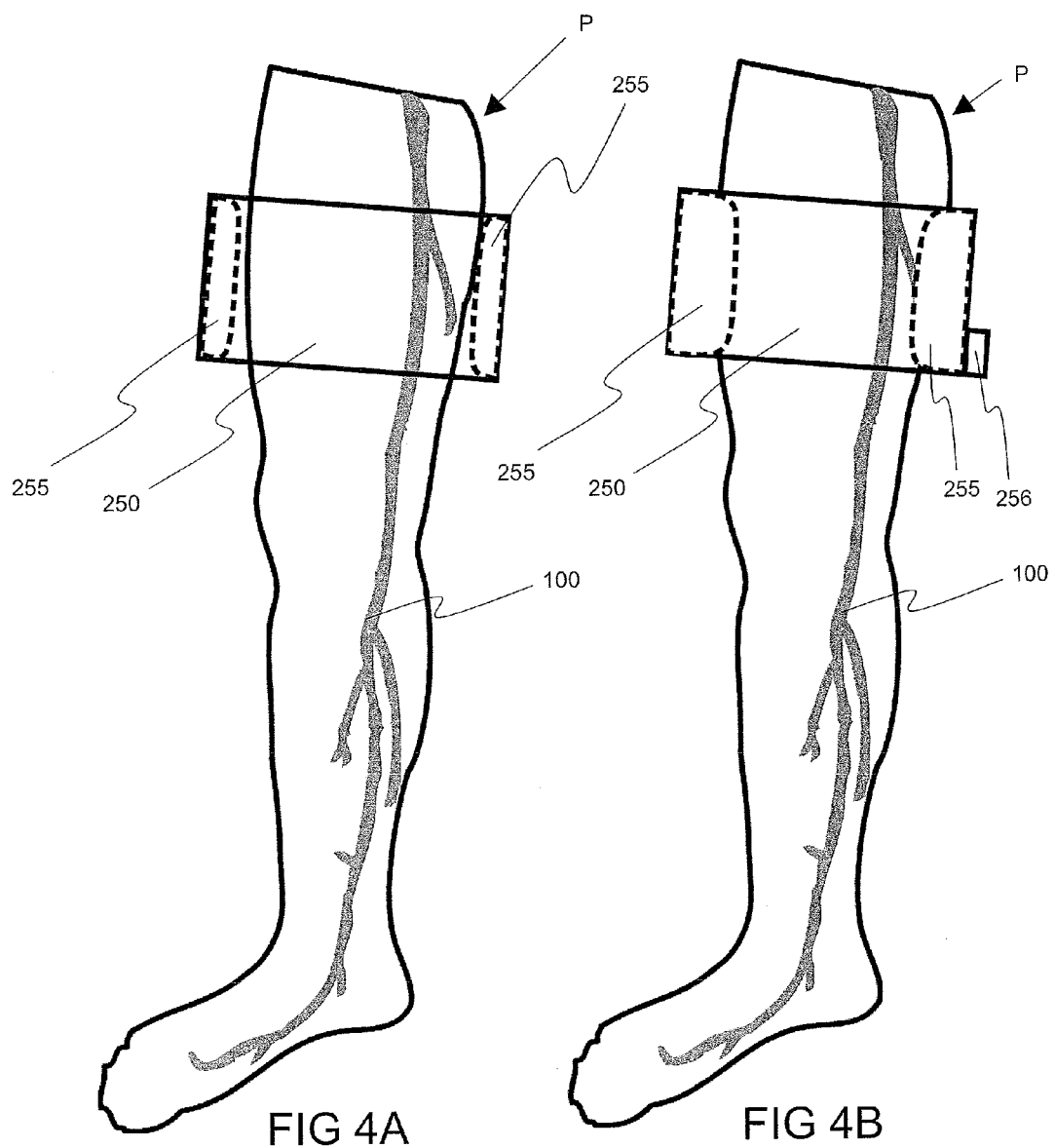
FIG. 4A is a schematic view of an example pressure applying cuff applied around the thigh of a patient.
FIG. 4B is a schematic view of the pressure applying cuff of FIG. 4A illustrating an internal cuff in an expanded state.

FIGS. 4A and 4B illustrate an example in situ vessel modification via placement of a pressure-applying cuff around a patient's thigh, shown in a deflated and inflated state, respectively. Cuff 250 can be placed around patient P's thigh such that in situ vein 100, typically a saphenous vein, is modified due to an increase in internal blood pressure caused when cuff 250 is inflated. Cuff 250 can be placed proximate the segment of vein 100 to be harvested or at a location superior or inferior to the segment location. An inflatable bladder 255, such as a bladder similar to those used to surround a patient's upper arm to measure blood pressure, is incorporated into cuff 250 and configured to surround the thigh of patient P. Bladder 255 is further configured to expand and contract, manually or automatically, such as to apply and remove a force, respectively, to patient P's thigh. In some embodiments, bladder 255 is expanded at night time or otherwise during sleep periods. The force applying inflations are repeated, e.g. once a day or once every other day. The modification process is continued for a specified period of time required to achieve the desired remodeling of vein 100. Alternatively, cuff 250 can be activated (e.g. bladder 255 inflated) at shorter and/or more frequent intervals, for example, bladder 255 is inflated every five minutes throughout the entire day or a portion of the day, for a specified period of time, such as 30 seconds. Inflatable bladder 255 can be inflated automatically such as via an electronically controlled air pumping system, or manually through squeezing of an elastomeric bulb and inflation tube, not shown but similar to those used in blood pressure measurement cuffs. In some embodiments (e.g., as in the example illustrated in FIG. 4B), pump 256, typically connected to a source of power and an electronic controller, both not shown, inflates inflatable bladder 255 via injection of a fluid, for example, air; nitrogen; helium; water; saline; and combinations of these, applying force around patient P's thigh and causing a pressure elevation in and/or around vein 100. Bladder 255 is deflated by withdrawal of the fluid, pumping in the opposite direction, such as into a reservoir, not shown.

Generally, normal pressure in vein 100, i.e. pressure prior to inflation of cuff 250, is much less than arterial blood pressure. As has been described above, elevated pressures as described herein used to modify a vein, i.e. pressure achieved subsequent to inflation of cuff 250, can range up to patient's normal expected arterial blood pressure (e.g. blood pressure in a coronary artery of the heart or in an artery of the leg), or to a higher level. Typical pressure increases include but are not limited to: an increase to at least 50 mmHg; an increase to at least 80 mmHg; or an increase to at least 100 mmHg.

In some embodiments, cuff 250 is used to apply a vacuum around patient P's thigh. Bladder 255 is used to create a relative seal around the patient's thigh, and pump 256 is a vacuum pump used to create a negative pressure on the skin surrounding bladder 255. This applied vacuum can modify the blood pressures and/or effect of blood pressures within vein 100, such as to cause a modification described herein.

The application of pressure can be steady or variable over time, such as a pulsatile pressure regimen. The pressure waveform can be of any shape and can be periodic or not.

FIG. 5 illustrates a vein modification via delivery of an agent to an in situ vessel, such as a vein in a patient's leg. Syringe 260, including needle 261 shown accessing the vessel wall of vein 100, can be used to deliver a drug or other agent, agent 265, to vein 100, typically a saphenous vein. The agent can be delivered to a segment of vein 100 to be harvested, and/or to a location external to the segment to be harvested. Agent 265 can be delivered intraluminally, into the wall of vein 100, or to an area proximate but external to vein 100. Agent 265 can be delivered via at least one bolus injection. Alternatively or additionally, agent 265 can be delivered over time, either intermittently or continuously, at constant or variable flow rates. For example, agent 265 can be administered to patient P daily or weekly. In some embodiments, agent 265 can be delivered continuously via a pump, not shown, but similar to a skin attached infusion pump such as that described in U.S. patent Ser. No. 10/128,205, entitled "Dispenser for Patient Infusion Device" and filed on Apr. 23, 2002, the contents of which are hereby incorporated herein by reference in their entirety. Non-limiting examples of agent 265 can include: thrombotic agents; anti-thrombotic agents; anti-inflammatory agents; pro-inflammatory agents; cells such as stem cells; anti angiogenic agents; angiogenic agents; antifibrotic agents; fibrotic agents; cytostatic agents; antimitotic agents; pro-mitotic agents; other biological agents such as growth factors, cytokines, and antibodies; vasoactive agents; genetic transfection agents such as transfection factors, plasmids, and other gene vectors; and combinations of these.

Figure 6:
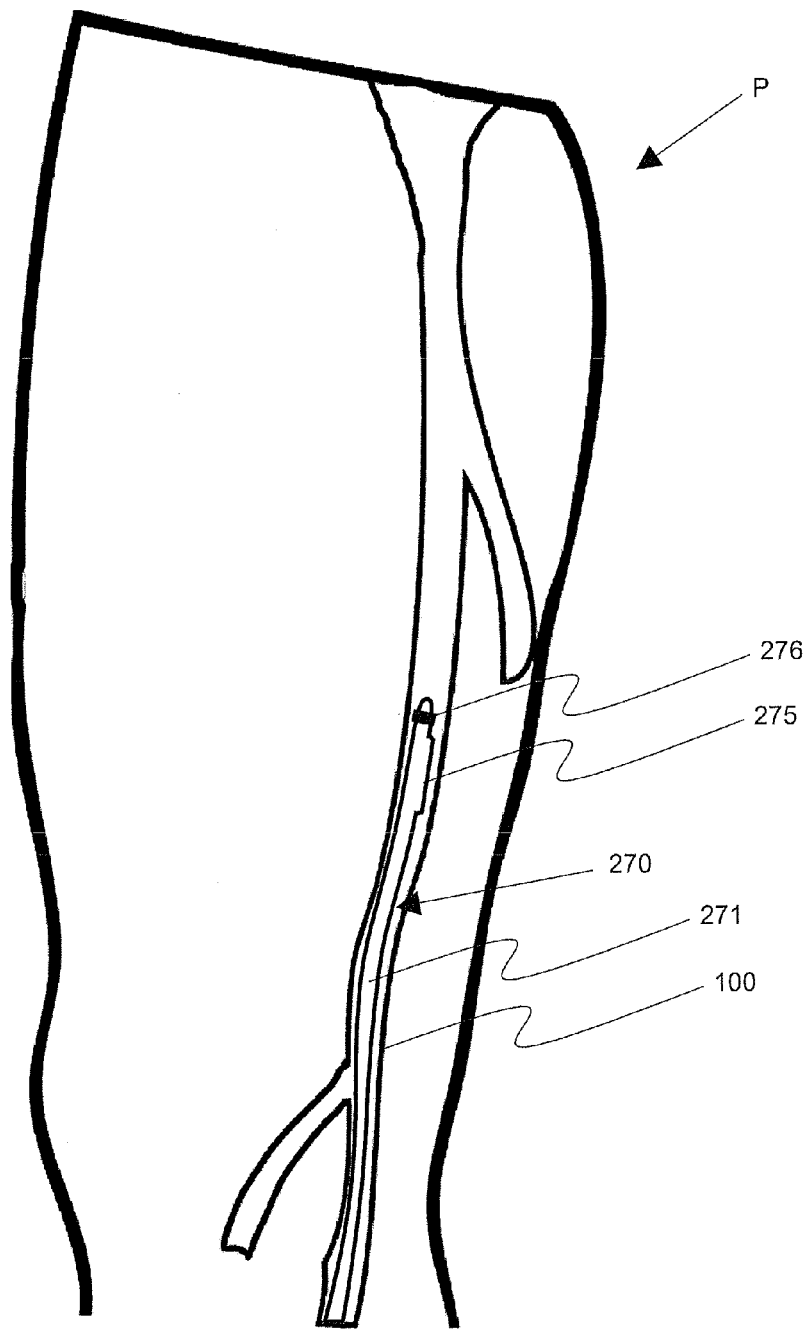
FIG. 6 is a schematic view of an example valve modifying device inserted into a vessel to be harvested.

FIG. 6 illustrates an example in situ vessel modification including the treatment of one or more venous valves. Modification of in situ vein 100 can occur, for example, through removal and/or disruption of one or more valves present in vein 100. The valves can be located in the segment of vein 100 to be harvested, and/or at a location external to that segment. As illustrated, in some embodiments, catheter 270 can include both ablation element 276 and functional element 275 on the distal end of shaft 271. Ablation element 276 can ablate or otherwise apply energy to the venous valve(s) via one or more forms of energy such as radiofrequency (RF) energy and/or ultrasound energy. Functional element 275 can include: cutting means, such as scissors or scalpels; a grasper; an abrasive element; and one or more other tools configured to remove, modify or disrupt one or more venous valves. Ablation element 276 and functional element 275 can be used separately or in combination, either simultaneously or sequentially. For example, ablation element can ablate tissue (e.g. a valve), followed by cutting the tissue using functional element 275 or vice versa. In addition, it is envisioned that modification of the venous valve(s) can create scar tissue and/or promote angiogensis, resulting in tissue regrowth where the newly grown tissue displays properties desirable for harvesting vein 100 and/or uses of vein 100 in various medical procedures, such as an AVG used in a bypass procedure, described herein.

The location of one or more venous valves can be identified using one or more of: an ultrasound imager; an X-ray; a fluoroscope; a CT scanner; and an MRI. Upon viewing the generated image, vein 100 can be chosen based on the location of one or more venous valves, such as to avoid one or more venous valves. Alternatively or additionally, generated images can be used in modifying the venous valves, such as prior to (e.g. for assessment and location), during (e.g. to guide tools), or after (e.g. to confirm adequate treatment) the valve modifying procedure.

Figure 7:
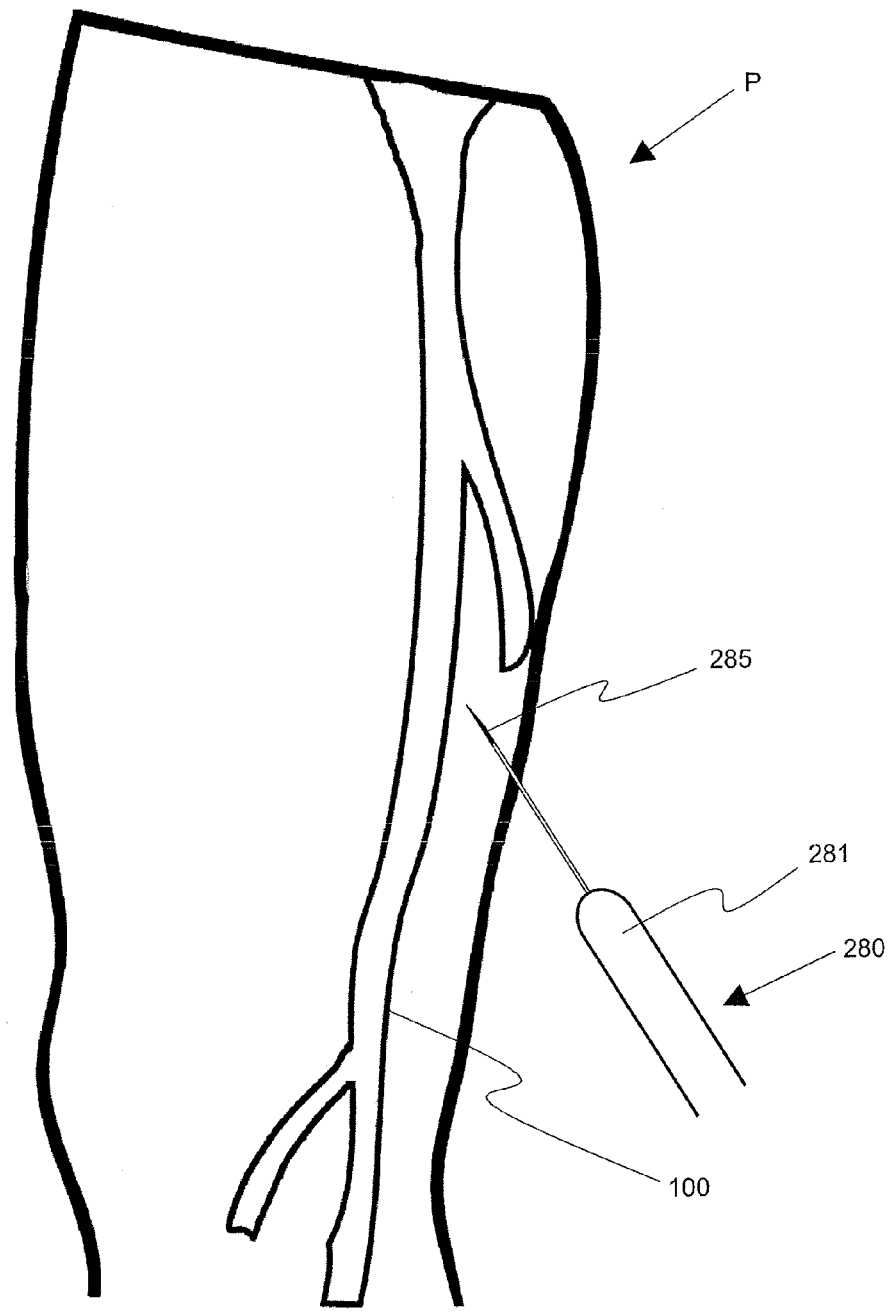
FIG. 7 is a schematic view of an example vessel modifying device accessing the walls of a vessel to be harvested.

FIG. 7 illustrates an example in situ vessel modification including the creation of scar tissue in the in situ vessel. Modification of in situ vein 100, typically a saphenous vein, can include a modification within, on, or outside the wall of vein 100, e.g. such that a scar is created proximate the adventitia. As illustrated, in some embodiments, tool 280, comprising handle 281 and functional tip 285, can be used to apply energy proximate vein 100 via functional tip 285. Energy can be applied within the lumen (e.g. against the inner wall of vein 100), within the wall of vein 100, on the outside of the wall of vein 100, or external to vein 100. Energy can be applied in a single treatment or multiple treatments. Energy can be applied continuously or intermittently, at constant or variable energy levels. In some embodiments, energy can be applied to cause one or more resultant scars. In some embodiments, energy is applied at locations proximate to each of the ends of the segment to be harvested, such as to modify the ends for a subsequent anastomotic connection. In some embodiments, energy is applied at locations proximate one or more sidebranches of vein 100 such as to modify the tissue in these areas.

The type of energy applied can be selected from the group consisting of: radiofrequency; microwave; ultrasound; chemical; laser; mechanical; and combinations of these. Similar to the vessel modifications described in reference to FIG. 6 hereabove, it is envisioned that the creation of scar tissue can promote angiogensis, resulting in tissue regrowth where the newly grown tissue can display properties desirable in various medical procedures requiring a harvested vessel.

In some embodiments, tool 285 can be used to apply a vacuum to the tissue proximate vein 100, such as wherein tip 285 is a vacuum port fluidly attached to a vacuum pump, not shown. This applied vacuum can modify the blood pressures within vein 100, such as to cause a modification in accordance with the methods described herein.

Figure 8:
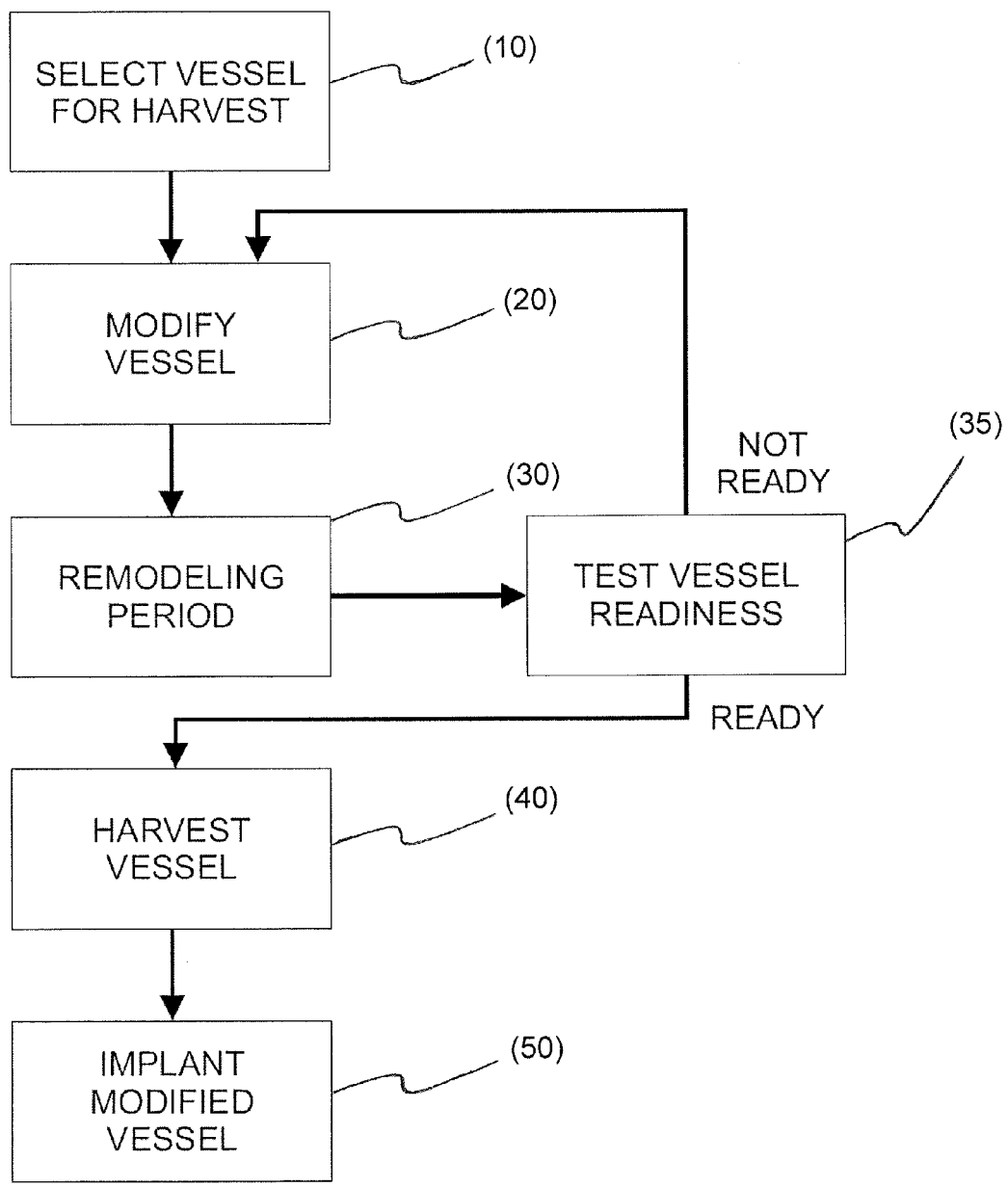
FIG. 8 is a flow chart depicting an example method for implanting a harvested vessel, including modifying the vessel prior to harvesting and confirming readiness of the graft for implantation.

FIG. 8 depicts an example method of creating a modified vessel for use in a medical procedure, for example a modified vein for use in a bypass procedure, similar to the method described in FIG. 1 hereabove, that includes an additional step of testing the readiness of the in situ vessel prior to harvesting. For example, a vessel can be selected for harvest (10), such as those as have been described hereabove and typically a vein located in a limb of a patient. The selected vessel can be modified (20), in situ, where the modification can be performed using one or more of the various devices and methods described herein. The vessel then undergoes a remodeling period. (30) The modified and remodeled vessel can be tested in situ as to the vessel's readiness to harvest. (35) If the vessel is determined ready to harvest, a clinician can proceed to harvesting the vessel (e.g., vein) (40). However, if the vein is determined to require further modification and remodeling, the vessel can undergo repeated further be modification (20) and remodeling (30) until the desired vessel properties are achieved.

Testing the vessel or vessel segment's readiness to harvest (35) can include the performance of one or more diagnostic tests of the segment of the vessel to be removed and/or of a location proximate that segment. The diagnostic tests can include creating an image of the vessel, such as an image created using X-ray or fluoroscopy; CT-scan; ultrasound; MRI and the like. Intravascular imaging devices such as intravascular ultrasound or OCT can be used to create detailed images of the vessels wall, such as to determine if a vein has undergone transformations mimicking the characteristics of an artery. Additionally or alternatively, a number of diagnostic tests or readings can be performed including but not limited to: pressure measurement; stiffness measurement; compliance measurement; distensibility measurement; blood tests; pH measurement; temperature measurement; assessment of inflammation or inflammatory response; tissue impedance measurements; and assessment of angiogenesis. Alternatively or additionally, a diagnostic test can be performed at other times, such as prior to vessel section (10) or modification (20), such as to assist in vessel selection or determination of one or more parameters used to modify the selected vessel, such as the various vessel modification parameters listed in reference to FIGS. 1 through 7 hereabove.

As stated above, if the outcome of vessel testing for readiness (35) is that the vessel segment is not ready for harvest, the vessel modification (20) can be re-performed and/or adjusted and re-performed. Adjustments can include one or more of: increasing pressure levels applied to the vessel such as to increase blood pressure within the vessel; adjusting energy delivery levels to or around the vessel; providing additional or alternative flow occluding or flow limiting implants within the vessel or a sidebranch of the vessel; and the like.

Next, the vessel can be harvested. (40) Subsequent to harvesting the vessel, the vessel can undergo various treatments, for example, a fiber matrix or other covering can be applied, such as via an electrospinning process, as has been described herein.

The modified vessel can then be implanted (50) during a medical procedure, for example a modified vein implanted between a source of oxygenated blood and an occluded artery in a bypass procedure.

Figure 9:
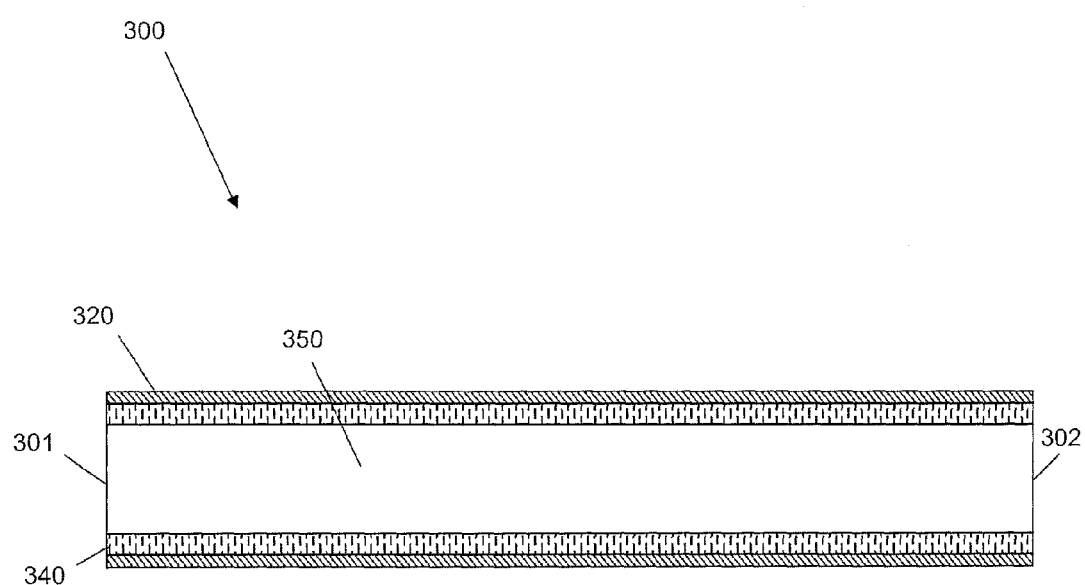
FIG. 9 is a side sectional view of an example graft device including a fiber matrix circumferentially placed around a harvested vessel.

FIG. 9 illustrates a side sectional view of an example harvested vessel segment including a restrictive fiber matrix covering. Graft device 300 typically includes tubular member, conduit 340, circumferentially surrounded by fiber matrix 320. Conduit 340 has been modified, prior to harvesting, as has been described in detail hereabove, and is typically a segment of harvested vein that has been exposed to elevated pressures over time or another modification. Fiber matrix 320 can be a restrictive matrix, typically including one or more polymers. The matrix can include permanent materials, bioerodible materials, or combinations of these. Graft device 300 includes a first end 301 and a second end 302, and is typically configured to be placed between a first body location and a second body location of a patient. Graft device 300 includes lumen 350 from first end 301 to second end 302, such as to carry blood when graft device 300 is connected between two blood vessels. Fiber matrix 320 is typically applied using an electrospinning process, as has been described hereabove. The electrospinning process can be performed in an operating room, such as when conduit 340 is a harvested saphenous vein graft to be anastomosed between the aorta and a location on a diseased coronary artery distal to an occlusion. End to side anastomotic connections are typically used to attach device 300 to the aorta and to a disease artery, distal to the occlusion. Alternatively, a side to side anastomosis can be used, such as to attach an end of device 300 to multiple arteries in a serial fashion. Alternate sources of arterial blood can be attached to device 300, such as an internal mammary artery (IMA), or another graft, such as another device 300, typically with an end to side anastomosis.

Fiber matrix 320 can be processed in a way specific to a patient morphological or functional parameter. These parameters can be selected from the group consisting of: vessel size such as diameter, length, and/or wall thickness; taper or other geometric property of a harvested vessel or vessel intended for anastomotic attachment; size and location of one or more sidebranch ostium or antrum within the harvested vessel; patient age or sex; vessel elasticity or compliance; vessel vasculitis; vessel impedance; specific genetic factor or trait; and combinations of these. Conduit 340 is preferably free of any metal or magnetic material (in embodiments in which the matrix is deposited via electrospinning), such as metal clips used to ligate a sidebranch of a harvested saphenous vein.

Fiber matrix 320, when used for AVGs, can be processed in a way to achieve a certain blood flow rate or shear stress within the treated AVG. In a typical configuration, shear stress within the arterial vein graft is between 2-30 dynes/$cm^2$, for example 12-20 dynes/$cm^2$. Fiber matrix 320 can be processed in a way to control the oxygen, nutrients, or cellular permeabilities between the extravascular tissues and the abluminal surface of the treated vein graft. Such permeabilities depend on the polymer chemical and physical properties, the pore size distribution, porosity, and pore interconnectivity. In a non-limiting example, cellular permeability can be selectively restricted to reduce leukocyte infiltration across the deposited fiber matrix with pore sizes smaller than seven microns and porosities between 50% and 95%. Generally, oxygen, nutrients, and cellular (e.g., endothelial cells, endothelial progenitor cells, etc.) permeability are required to improve the treated vein graft in vivo remodeling and healing process. To this end, the pore size range is typically between 10 microns and 1000 microns, for example between 200 microns and 500 microns, and the porosity range typically between 50% and 95%, for example between 60% and 90%. The pores preferably are highly interconnected so that a relatively straight path along the radial direction of the fiber matrix can be traced from most of the pores across the total thickness of the matrix. The polymer is typically hydrophilic.

The devices described herein can have one or more parameters customized (e.g., easily customized) to a parameter of the harvested vessel and/or another patient parameter. The fiber matrix can be customized to a harvested vessel parameter such as geometry, such as to reduce the vein internal diameter to produce desired flow characteristics. The fiber matrix can be customized to a target vessel parameter (e.g., the aorta and diseased artery), such as to be compatible with vessel sizes and/or locations. The fiber matrix can be modified to simplify or otherwise improve the anastomotic connections, such as to be reinforced in the portion of the device that is anastomosed (e.g., portion where suture and/or clips pass through) and/or to protrude beyond the length of the tubular member and overlap other members connected to the graft device. The devices described herein can be made to a wide array of lengths during the procedure, without the need for cutting, such as the cutting of a stent device, which might create dangerously sharp edges. The fiber matrix is applied to the tubular member in a controlled, repeatable manner, by an apparatus such as an electrospinning instrument. The ends of the fiber matrix are atraumatic, avoiding tissue damage at the anastomotic sites. In addition, the fiber matrices described herein can be easily and atraumatically removable, such as to apply another fiber matrix.

Alternatively or additionally, radial constriction of conduit 340 can be achieved with stent devices placed over the vein prior to anastomosing the graft to the targeted vessels.

While some example embodiments of the devices and methods have been described in reference to the environment in which they were developed, they are merely for illustrative purposes. Modification or combinations of the above-described assemblies, other embodiments, configurations, and methods for carrying out the invention, and variations of aspects of the methods and systems described herein that are obvious to those of skill in the art are intended to be within the scope of the claims. In addition, where this application has listed the steps of a method or procedure in a specific order, it can be possible, or even expedient in certain circumstances, to change the order in which some steps are performed, and it is intended that the particular steps of the method or procedure claim set forth herebelow not be construed as being order-specific unless such order specificity is expressly stated in the claim.

We claim:

1. A method of performing a medical procedure, the method comprising:
    modifying an in situ vessel;
    removing at least one segment of the modified in situ vessel;
    applying a restrictive member about the at least one removed, modified in situ vessel segment to produce a covered graft device; and
    implanting the covered graft device in a patient;
wherein the in situ vessel modification is performed at least one week prior to removing the at least one vessel segment.

2. The method of claim 1 wherein the restrictive member comprises a restrictive fiber matrix.

3. The method of claim 1 wherein the restrictive member comprises a stent.

4. The method of claim 1 further comprising:
    fluidly connecting a first portion of the covered graft device to a source of blood flow; and
    fluidly connecting a second portion of the covered graft device to an artery.

5. The method of claim 1 wherein the in situ vessel comprises a vein.

6. The method of claim 1 wherein the in situ vessel is selected from the group consisting of: vein, artery, urethra, intestine, esophagus, trachea, bronchi, ureter, duct, fallopian tube, and combinations of these materials.

7. The method of claim 1 wherein the modification comprises increasing the pressure within the in situ vessel.

8. The method of claim 7 wherein the pressure increase comprises an increase to at least 50 mmHg.

9. The method of claim 7 wherein the pressure increase comprises a pressure that is varied over time.

10. The method of claim 7 wherein the pressure is incrementally increased over time.

11. The method of claim 1 wherein the modification comprises applying a pressure applying cuff to the patient's skin proximate the in situ vessel.

12. The method of claim 11 wherein the cuff further comprises an inflatable bladder.

13. The method of claim 12 further comprising intermittently inflating the inflatable bladder such that pressure within the in situ vessel is intermittently elevated.

14. The method of claim 11 wherein the pressure applying cuff causes the pressure within the in situ vessel to increase.

15. The method of claim 1 wherein the modification comprises applying a vacuum around the in situ vessel.

16. The method of claim 1 wherein the modification comprises implanting a mechanical scaffold within the in situ vessel.

17. The method of claim 1 wherein the modification comprises implanting a flow occluding device proximate to the in situ vessel.

18. The method of claim 17 wherein the modification comprises implanting the flow occluding device within a sidebranch proximate the in situ vessel.

19. The method of claim 17 wherein the flow occluding device is constructed and arranged to at least partially occlude flow in a lumen of a vessel.

20. The method of claim 1 wherein the modification comprises ligating at least one vessel sidebranch.

21. The method of claim 1 wherein the modification comprises application of energy to the in situ vessel.

22. The method of claim 21 wherein the energy comprises energy selected from the group consisting of: radiofrequency, ultrasound, chemical, laser, mechanical, and combinations of these.

23. The method of claim 21 wherein the application of energy promotes angiogenesis.

24. The method of claim 1 wherein the modification comprises modifying one or more valves of the in situ vessel.

25. The method of claim 1 wherein the modification promotes angiogenesis.

26. The method of claim 1 wherein the modification comprises delivering an agent into the in situ vessel.

27. A method of performing a medical procedure, the method comprising:
    removing at least one segment of a vessel that has been modified in situ at least one week prior to the removing of the vessel segment;
    applying a restrictive member about the at least one vessel segment to produce a covered graft device; and
    implanting the covered graft device in a patient.

28. The method of claim 27 wherein the restrictive member comprises a restrictive fiber matrix.

29. The method of claim 27 wherein the restrictive member comprises a stent.

30. The method of claim 27 wherein the in situ vessel comprises a vein.

31. The method of claim 27 wherein the modification comprises increasing the pressure within the in situ vessel.

32. The method of claim 31 wherein the pressure increase comprises an increase to at least 50 mmHg.

33. The method of claim 31 wherein the pressure increase comprises a pressure that is varied over time.

34. The method of claim 31 wherein the pressure is incrementally increased over time.

35. The method of claim 27 wherein the modification comprises applying a pressure applying cuff to the patient's skin proximate the in situ vessel.

36. The method of claim 35 wherein the cuff further comprises an inflatable bladder.

37. The method of claim 36 further comprising intermittently inflating the inflatable bladder such that pressure within the in situ vessel is intermittently elevated.

38. The method of claim 35 wherein the pressure applying cuff causes the pressure within the in situ vessel to increase.

* * * * *